(12) United States Patent
Casey et al.

(10) Patent No.: US 11,460,408 B2
(45) Date of Patent: Oct. 4, 2022

(54) METHOD OF GEOCHEMICAL CHARACTERIZATION, PRODUCTION ALLOCATION, AND MONITORING USING TRACE AND ULTRA-TRACE ELEMENT ANALYSIS

(71) Applicant: University of Houston System, Houston, TX (US)

(72) Inventors: John F. Casey, Sugar Land, TX (US); Yongjun Gao, Pearland, TX (US); Weihang Yang, Houston, TX (US); Jiaxuan Li, Houston, TX (US)

(73) Assignee: UNIVERSITY OF HOUSTON SYSTEM, Houston, TX (US)

( * ) Notice: Subject to any disclaimer, the term of this patent is extended or adjusted under 35 U.S.C. 154(b) by 45 days.

(21) Appl. No.: 17/122,293

(22) Filed: Dec. 15, 2020

(65) Prior Publication Data

US 2021/0181117 A1  Jun. 17, 2021

Related U.S. Application Data

(60) Provisional application No. 62/949,311, filed on Dec. 17, 2019.

(51) Int. Cl.
*G01N 21/73* (2006.01)
*H01J 49/10* (2006.01)
*G01N 27/62* (2021.01)
*G01N 1/44* (2006.01)

(52) U.S. Cl.
CPC .............. *G01N 21/73* (2013.01); *G01N 1/44* (2013.01); *G01N 27/62* (2013.01); *H01J 49/105* (2013.01)

(58) Field of Classification Search
CPC .......... G01N 21/73; G01N 1/44; G01N 27/62; H01J 49/105
USPC ................................. 250/281, 282, 288, 283
See application file for complete search history.

(56) References Cited

U.S. PATENT DOCUMENTS

| | | | |
|---|---|---|---|
| 2015/0272119 A1* | 10/2015 | Nussaume | A01N 41/12 504/307 |
| 2018/0334553 A1* | 11/2018 | Fleury | C08C 19/28 |
| 2019/0239537 A1* | 8/2019 | Andersen | A23C 9/1427 |

OTHER PUBLICATIONS

New Approaches in Sample Preparation and Precise Multielement Analysis of Crude Oils and Refined Petroleum Products Using Single-Reaction-Chamber Microwave Digestion and Triple-Quadrupole ICP-MS, Spectroscopy, 31(10) pp. 11-22, Oct. 2016 (Year: 2016).*

(Continued)

*Primary Examiner* — Nicole M Ippolito
(74) *Attorney, Agent, or Firm* — Carter, DeLuca & Farrell LLP; George Likourezos

(57) ABSTRACT

A system for geochemical characterization of a sample includes a closed reaction chamber configured to perform a high temperature and high-pressure acid digestion test, a spectrometry system configured for performing trace element analysis, and a controller. The controller includes a processor and a memory. The memory includes instructions stored thereon, which, when executed by the processor, cause the system to mineralize the sample based on a microwave process using the closed reaction chamber, and perform trace element analysis on the mineralized sample by the spectrometry system.

20 Claims, 25 Drawing Sheets

(56) References Cited

OTHER PUBLICATIONS

Casey, J. F., Gao, Y., Yang, W., Thomas, R. (2016) New approaches in sample preparation and precise multielement analysis of crude oils and refined petroleum products using single-reaction-chamber microwave digestion coupled with Triple-Quadrupole ICP-MS, Spectroscopy 31 (10), 1-10.

Yang, W., Casey, J. F., Gao, Y., Li, J. (2019) A new method of geochemical allocation and monitoring of commingled crude oil production using trace and ultra-trace multi-element analyses, Fuel 241, 347-359.

Yang, W., Casey, J. F., Gao, Y. (2017) A new sample preparation method for crude or fuel oils by mineralization utilizing single reaction chamber microwave for broader multi-element analysis by ICP techniques, In Fuel, vol. 206, 2017, pp. 64-79, ISSN 0016-2361.

\* cited by examiner

| Analytes | S1[a] | RSD1[b] | S2 | RSD2 | S3 | RSD3 | S4 | RSD4 | S5 | RSD5 | Mix | RSD_Mix |
|---|---|---|---|---|---|---|---|---|---|---|---|---|
| Na | 8886 | 1.7 | 30,284 | 3.4 | 19,881 | 5.7 | 14,517 | 1.9 | 48,593 | 0.5 | 21,167 | 1.1 |
| Mg | 177 | 9.8 | 260 | 2.7 | 1008 | 0.8 | 321 | 8.0 | 2404 | 0.4 | 615 | 4.4 |
| Sc | 1.94 | 1.5 | 1.53 | 3.2 | 0.01 | 0.8 | 2.22 | 0.8 | 0.63 | 1.5 | 1.39 | 0.6 |
| Ca | 2753 | 3.2 | 2894 | 6.6 | 5706 | 1.0 | 5088 | 2.4 | 7228 | 1.5 | 3982 | 1.8 |
| Ti | 2542 | 1.9 | 626 | 3.8 | 29.1 | 2.1 | 18.1 | 17.1 | 51.9 | 7.4 | 951 | 1.6 |
| V | 84,584 | 1.4 | 68,838 | 3.3 | 15.9 | 7.7 | 92,799 | 0.4 | 10,543 | 1.0 | 59,030 | 0.6 |
| Mn | 24.1 | 8.9 | 10.8 | 0.6 | 1878 | 3.2 | 11.7 | 6.7 | 375 | 2.3 | 440 | 3.1 |
| Fe | 5923 | 1.8 | 11,140 | 3.6 | 697,338 | 1.4 | 567 | 12.9 | 21,623 | 0.6 | 147,366 | 0.4 |
| Co | 1181 | 7.2 | 2297 | 5.7 | 23.7 | 3.3 | 19.0 | 2.3 | 164 | 3.9 | 942 | 1.7 |
| Ni | 74,007 | 0.9 | 61,223 | 3.1 | 1352 | 7.3 | 52,238 | 0.9 | 5316 | 2.8 | 47,109 | 0.8 |
| Cu | 43.1 | 6.7 | 22.4 | 0.3 | 1738 | 4.9 | 363 | 3.9 | 58.7 | 5.3 | 426 | 3.2 |
| Zn | 1255 | 2.9 | 943 | 7.0 | 2694 | 2.6 | 738 | 3.1 | 1988 | 2.9 | 1458 | 1.2 |
| Ga | 292 | 5.8 | 118 | 6.7 | 3.59 | 4.4 | 9.20 | 4.2 | 9.14 | 2.6 | 123 | 4.0 |
| Sr | 15.6 | 0.3 | 71.8 | 3.3 | 25.8 | 2.3 | 75.4 | 0.2 | 91.0 | 0.2 | 47.7 | 1.5 |
| Y | 8.07 | 7.2 | 1.78 | 8.9 | 0.35 | 18.8 | 0.25 | 12.7 | 0.88 | 6.0 | 2.96 | 1.2 |
| Zr | 30.8 | 7.1 | 8.51 | 10.5 | 1.65 | 2.7 | 4.49 | 13.0 | 5.13 | 6.3 | 12.5 | 1.5 |
| Mo | 404 | 6.3 | 327 | 6.3 | 23.4 | 2.2 | 60.5 | 3.8 | 12.5 | 8.8 | 218 | 0.5 |
| Cd | 1.91 | 7.9 | 167 | 5.8 | 1.51 | 10.8 | 1.44 | 15.0 | 5.79 | 9.7 | 45.0 | 1.2 |
| Ba | 45.3 | 3.2 | 489 | 3.7 | 22.0 | 9.1 | 1516 | 0.6 | 27.2 | 9.9 | 359 | 1.6 |
| Pb | 30.8 | 9.2 | 141 | 7.4 | 2911 | 8.9 | 6.47 | 20.3 | 24.7 | 10.1 | 672 | 2.6 |

[a] The average mass fractions of all the analytes in the five end-member oils and the commingled oils of the three replicated tests, respectively (Unit: ng/g);
[b] ERSD (experimental relative standard deviations of the 3 analyses) ($1\sigma$, n = 3) of all the analytes in the five end-member oils and the commingled oils of the three replicated tests, respectively (Unit: %);
[c] The unit for sulfur is wt.%.
The units are in %

FIG. 19

| Oils | True | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|
| S1 | 29.9 | 33.6 | 29.9 | 30.1 | 30.5 | 30.7 | 30.9 | 31.3 | 31.3 | 31.4 | 31.3 | 31.1 | 30.4 | 30.1 | 29.9 | 29.9 |
| S2 | 25.3 | 22.5 | 27.1 | 24.7 | 24.6 | 24.4 | 24.0 | 23.9 | 23.8 | 23.7 | 24.2 | 24.4 | 25.1 | 25.7 | 25.8 | 25.9 |
| S3 | 19.8 | 17.6 | 20.1 | 20.1 | 20.0 | 20.2 | 20.2 | 20.2 | 20.2 | 20.2 | 20.2 | 20.2 | 20.3 | 20.3 | 20.3 | 20.6 |
| S4 | 15.1 | 14.5 | 14.7 | 16.2 | 15.9 | 15.4 | 15.0 | 14.7 | 14.7 | 14.7 | 14.5 | 14.5 | 14.4 | 14.2 | 14.3 | 14.2 |
| S5 | 10.0 | 11.8 | 8.1 | 8.8 | 9.1 | 9.3 | 9.9 | 10.0 | 10.0 | 10.1 | 9.8 | 9.8 | 9.7 | 9.6 | 9.6 | 9.4 |

The units are in %

FIG. 20

| Oils | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|
| S1 | 12.4 | 0.2 | 0.9 | 2.1 | 2.8 | 3.6 | 4.7 | 4.6 | 5.0 | 5.0 | 4.3 | 2.0 | 0.9 | 0.3 | 0.03 |
| S2 | 11.1 | 7.0 | 2.5 | 3.0 | 3.7 | 5.4 | 5.8 | 5.9 | 6.2 | 4.5 | 3.8 | 0.9 | 1.6 | 1.9 | 2.1 |
| S3 | 11.2 | 1.7 | 1.7 | 1.0 | 2.4 | 2.0 | 2.0 | 2.0 | 2.0 | 2.1 | 2.2 | 2.5 | 2.6 | 2.7 | 4.1 |
| S4 | 3.5 | 2.1 | 7.8 | 5.5 | 2.2 | 0.6 | 2.2 | 1.7 | 2.6 | 3.7 | 3.6 | 4.0 | 5.5 | 5.1 | 5.3 |
| S5 | 18.4 | 18.7 | 11.4 | 8.8 | 6.8 | 0.4 | 0.1 | 0.1 | 0.7 | 2.1 | 2.2 | 2.5 | 3.6 | 3.4 | 5.5 |
| Ave.[a] | 11.3 | 5.9 | 4.9 | 4.1 | 3.6 | 2.4 | 3.0 | 2.9 | 3.3 | 3.5 | 3.2 | 2.4 | 2.8 | 2.7 | 3.4 |
| SD[b] | 5.3 | 7.6 | 4.5 | 3.1 | 1.9 | 2.1 | 2.3 | 2.3 | 2.2 | 1.3 | 1.0 | 1.1 | 1.8 | 1.8 | 2.3 |

[a] Average calculation accuracies of the five end-member oils for specific numbers of analytes used in calculations;
[b] SDs (1σ, n = 5) of the calculation accuracies of the five end-member oils for certain numbers of analytes.

The units are in %

FIG. 21

| Oils | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|
| S1 | 2.4 | 1.4 | 1.9 | 1.9 | 1.9 | 2.1 | 1.6 | 1.6 | 1.6 | 1.6 | 1.4 | 1.3 | 1.1 | 1.0 | 1.1 |
| S2 | 5.0 | 3.3 | 1.8 | 1.9 | 2.0 | 2.2 | 2.3 | 2.4 | 2.8 | 2.7 | 2.5 | 2.4 | 1.5 | 1.5 | 1.5 |
| S3 | 3.0 | 0.5 | 0.8 | 0.6 | 0.6 | 0.7 | 0.8 | 0.7 | 0.9 | 0.9 | 0.9 | 0.9 | 1.1 | 1.1 | 1.0 |
| S4 | 2.9 | 4.2 | 3.1 | 3.1 | 3.2 | 3.4 | 3.1 | 3.1 | 2.2 | 2.2 | 2.4 | 2.4 | 2.3 | 2.4 | 2.4 |
| S5 | 6.7 | 4.5 | 4.1 | 3.8 | 3.9 | 2.5 | 2.7 | 2.9 | 3.1 | 3.1 | 3.2 | 3.3 | 3.5 | 3.7 | 3.7 |
| Ave.[a] | 4.0 | 2.8 | 2.3 | 2.3 | 2.3 | 2.2 | 2.1 | 2.1 | 2.1 | 2.1 | 2.1 | 2.1 | 1.9 | 1.9 | 1.9 |

[a] Average calculation uncertainties of the five end-member oils for certain numbers of analytes.
The units are in %

FIG. 22

| Oils | True | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|
| S1 | 29.9 | 29.8 | 29.8 | 29.7 | 29.9 | 29.6 | 29.6 | 29.7 | 29.7 | 29.7 | 29.7 | 29.8 | 29.8 | 29.8 | 29.9 | 29.9 |
| S2 | 25.3 | 26.3 | 26.4 | 26.3 | 26.3 | 26.1 | 26.2 | 25.9 | 26.3 | 25.9 | 25.9 | 25.9 | 25.9 | 25.9 | 25.9 | 25.9 |
| S3 | 19.8 | 21.4 | 21.5 | 21.5 | 21.5 | 21.3 | 21.1 | 20.8 | 20.9 | 20.6 | 20.6 | 20.6 | 20.6 | 20.6 | 20.6 | 20.6 |
| S4 | 15.1 | 21.8 | 14.0 | 14.1 | 14.1 | 13.7 | 13.7 | 13.7 | 13.9 | 13.9 | 14.1 | 14.1 | 14.2 | 14.2 | 14.2 |
| S5 | 10.0 | 0.7 | 8.2 | 8.4 | 8.2 | 9.3 | 9.3 | 9.6 | 9.7 | 9.8 | 9.8 | 9.6 | 9.5 | 9.5 | 9.5 | 9.4 |

The units are in %

FIG. 23

| Oils | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|
| S1 | 0.2 | 0.2 | 0.5 | 0.1 | 0.8 | 0.8 | 0.7 | 0.6 | 0.6 | 0.5 | 0.3 | 0.1 | 0.1 | 0.01 | 0.1 |
| S2 | 4.0 | 4.2 | 3.8 | 4.0 | 3.2 | 3.3 | 3.7 | 2.4 | 2.4 | 2.3 | 2.2 | 2.3 | 2.2 | 2.1 | 2.1 |
| S3 | 8.4 | 8.9 | 8.9 | 8.9 | 7.4 | 6.9 | 5.4 | 5.5 | 4.4 | 4.3 | 4.2 | 4.2 | 4.2 | 4.1 | 4.1 |
| S4 | 44.6 | 6.7 | 6.5 | 6.6 | 8.9 | 8.7 | 9.2 | 7.9 | 7.4 | 7.3 | 6.4 | 6.1 | 6.0 | 5.5 | 5.4 |
| S5 | 93.4 | 17.7 | 15.8 | 17.9 | 7.1 | 6.6 | 4.0 | 3.1 | 1.8 | 1.7 | 3.4 | 4.5 | 4.7 | 5.3 | 5.8 |
| Ave. | 30.1 | 7.5 | 7.1 | 7.5 | 5.5 | 5.3 | 4.6 | 3.9 | 3.3 | 3.2 | 3.3 | 3.4 | 3.4 | 3.4 | 3.5 |
| SD | 39.6 | 6.5 | 5.8 | 6.7 | 3.4 | 3.2 | 3.1 | 2.8 | 2.7 | 2.7 | 2.3 | 2.3 | 2.3 | 2.3 | 2.4 |

The units are in %

FIG. 24

| Oils | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|
| S1 | 0.8 | 0.9 | 0.9 | 0.8 | 0.9 | 1.0 | 1.0 | 1.0 | 1.1 | 1.1 | 1.1 | 1.1 | 1.0 | 1.1 | 1.0 |
| S2 | 1.0 | 1.2 | 1.1 | 1.2 | 1.3 | 1.4 | 1.4 | 1.3 | 1.4 | 1.4 | 1.5 | 1.5 | 1.5 | 1.5 | 1.5 |
| S3 | 1.1 | 1.3 | 1.3 | 1.3 | 1.4 | 1.1 | 1.0 | 1.0 | 1.0 | 0.9 | 0.9 | 0.9 | 1.0 | 1.0 | 1.0 |
| S4 | 2.9 | 2.0 | 2.0 | 2.1 | 2.3 | 2.4 | 2.5 | 2.4 | 2.5 | 2.5 | 2.4 | 2.5 | 2.6 | 2.5 | 2.4 |
| S5 | 77.2 | 6.0 | 5.5 | 5.6 | 3.6 | 3.9 | 3.7 | 3.7 | 3.8 | 3.7 | 3.6 | 3.8 | 3.6 | 3.6 | 3.7 |
| Ave. | 16.6 | 2.3 | 2.2 | 2.2 | 1.9 | 2.0 | 1.9 | 1.9 | 2.0 | 1.9 | 1.9 | 2.0 | 1.9 | 1.9 | 1.9 |

The units are in %

FIG. 25

| Oils | True | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|
| S1 | 29.9 | 28.7 | 30.3 | 29.5 | 29.8 | 29.7 | 29.7 | 29.7 | 29.5 | 29.5 | 29.6 | 29.7 | 29.7 | 29.8 | 29.7 | 29.8 |
| S2 | 25.3 | 26.0 | 26.0 | 26.1 | 26.2 | 25.7 | 25.7 | 25.7 | 25.8 | 25.8 | 25.8 | 25.7 | 25.7 | 25.6 | 25.8 | 25.8 |
| S3 | 19.8 | 20.6 | 20.7 | 20.6 | 20.7 | 20.6 | 20.6 | 20.6 | 20.6 | 20.6 | 20.6 | 20.6 | 20.6 | 20.6 | 20.6 | 20.6 |
| S4 | 15.1 | 13.9 | 13.8 | 13.8 | 13.9 | 14.0 | 13.9 | 13.9 | 14.0 | 14.1 | 14.1 | 14.3 | 14.3 | 14.3 | 14.3 | 14.3 |
| S5 | 10.0 | 10.8 | 9.2 | 10.0 | 9.5 | 9.9 | 10.0 | 10.1 | 10.1 | 10.0 | 9.9 | 9.7 | 9.7 | 9.7 | 9.6 | 9.5 |

The units are in %

FIG. 26

| Oils | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|
| S1 | 3.9 | 1.6 | 1.3 | 0.3 | 0.5 | 0.4 | 1.3 | 1.3 | 1.1 | 0.7 | 0.5 | 0.4 | 0.4 | 0.6 | 0.2 |
| S2 | 2.7 | 2.8 | 3.1 | 3.3 | 1.6 | 1.4 | 2.0 | 1.8 | 1.9 | 2.0 | 1.5 | 1.6 | 1.3 | 1.8 | 2.0 |
| S3 | 4.1 | 4.4 | 4.1 | 4.5 | 4.2 | 4.2 | 4.4 | 4.3 | 4.3 | 4.0 | 4.1 | 4.0 | 4.2 | 4.2 | 4.1 |
| S4 | 7.9 | 8.3 | 8.2 | 7.9 | 6.9 | 7.3 | 7.6 | 7.1 | 6.6 | 6.3 | 4.9 | 5.1 | 5.1 | 4.8 | 5.2 |
| S5 | 8.5 | 8.1 | 0.1 | 4.5 | 0.7 | 0.5 | 1.5 | 1.5 | 0.2 | 1.3 | 3.0 | 3.1 | 2.6 | 3.8 | 4.9 |
| Ave. | 5.4 | 5.1 | 3.4 | 4.1 | 2.8 | 2.7 | 3.4 | 3.2 | 2.8 | 2.9 | 2.8 | 2.9 | 2.7 | 3.0 | 3.3 |
| SD | 2.6 | 3.1 | 3.1 | 2.7 | 2.7 | 3.0 | 2.7 | 2.5 | 2.6 | 2.3 | 1.8 | 1.9 | 2.0 | 1.7 | 2.1 |

The units are in %

FIG. 27

| Oils | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|
| S1 | 4.5 | 1.4 | 1.2 | 1.0 | 1.1 | 1.1 | 1.1 | 1.1 | 1.0 | 1.1 | 1.0 | 1.1 | 1.2 | 1.0 | 1.0 |
| S2 | 0.9 | 1.2 | 1.2 | 1.4 | 1.3 | 1.4 | 1.3 | 1.4 | 1.4 | 1.4 | 1.4 | 1.3 | 1.3 | 1.4 | 1.5 |
| S3 | 0.6 | 0.8 | 0.8 | 0.8 | 0.8 | 0.9 | 0.9 | 0.9 | 1.0 | 1.0 | 1.0 | 0.9 | 1.0 | 0.9 | 1.0 |
| S4 | 1.6 | 2.2 | 2.4 | 2.3 | 2.2 | 2.5 | 2.7 | 2.3 | 2.4 | 2.5 | 2.4 | 2.2 | 2.4 | 2.4 | 2.3 |
| S5 | 12.1 | 5.7 | 5.4 | 5.6 | 5.1 | 3.4 | 3.6 | 3.4 | 3.9 | 3.6 | 3.8 | 3.9 | 3.4 | 3.4 | 3.8 |
| Ave. | 3.9 | 2.3 | 2.2 | 2.2 | 2.1 | 1.9 | 1.9 | 1.8 | 1.9 | 1.9 | 1.9 | 1.9 | 1.8 | 1.8 | 1.9 |

The units are in %

FIG. 28

| Oils | True | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|
| S1 | 29.9 | 31.6 | 30.3 | 27.8 | 28.2 | 29.5 | 29.6 | 30.2 | 29.6 | 29.9 | 30.1 | 30.0 | 30.0 | 29.8 | 29.8 | 29.8 |
| S2 | 25.3 | 29.1 | 29.0 | 28.7 | 28.2 | 25.9 | 25.0 | 24.8 | 25.2 | 25.0 | 25.4 | 25.4 | 25.3 | 25.7 | 25.8 | 25.8 |
| S3 | 19.8 | 18.9 | 19.8 | 21.3 | 21.0 | 19.5 | 19.5 | 19.3 | 19.6 | 19.4 | 20.1 | 20.1 | 20.4 | 20.4 | 20.7 | 20.6 |
| S4 | 15.1 | 12.1 | 13.1 | 15.8 | 15.8 | 15.4 | 16.0 | 15.7 | 15.9 | 15.8 | 14.6 | 14.6 | 14.5 | 14.3 | 14.3 | 14.3 |
| S5 | 10.0 | 8.3 | 7.8 | 6.4 | 6.8 | 9.7 | 9.8 | 10.0 | 9.7 | 9.9 | 9.8 | 9.9 | 9.8 | 9.6 | 9.4 | 9.5 |

The units are in %

FIG. 29

| Oils | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|
| S1 | 5.8 | 1.4 | 6.9 | 5.4 | 1.3 | 0.8 | 1.3 | 0.9 | 0.2 | 0.7 | 0.5 | 0.5 | 0.1 | 0.3 | 0.2 |
| S2 | 15.0 | 14.7 | 13.3 | 11.2 | 2.3 | 1.2 | 2.2 | 0.3 | 1.2 | 0.2 | 0.4 | 0.02 | 1.7 | 1.9 | 1.9 |
| S3 | 4.7 | 0.1 | 7.4 | 6.2 | 1.6 | 1.4 | 2.6 | 1.1 | 2.0 | 1.8 | 1.6 | 3.1 | 3.4 | 4.9 | 4.3 |
| S4 | 19.6 | 13.0 | 4.9 | 4.8 | 2.4 | 6.6 | 4.5 | 5.4 | 5.1 | 3.2 | 3.0 | 3.6 | 4.7 | 5.2 | 5.1 |
| S5 | 16.5 | 22.1 | 35.4 | 32.0 | 2.3 | 1.8 | 0.1 | 2.6 | 1.2 | 1.4 | 1.1 | 2.3 | 3.4 | 5.8 | 4.9 |
| Ave. | 12.3 | 10.3 | 13.6 | 12.0 | 2.0 | 2.3 | 2.1 | 2.1 | 2.0 | 1.5 | 1.3 | 1.9 | 2.6 | 3.6 | 3.3 |
| SD | 6.7 | 9.3 | 12.6 | 11.5 | 0.5 | 2.4 | 1.6 | 2.1 | 1.9 | 1.1 | 1.1 | 1.6 | 1.8 | 2.4 | 2.1 |

The units are in %

FIG. 30

| Oils | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|
| S1 | 2.2 | 2.2 | 2.3 | 0.9 | 1.2 | 1.0 | 1.0 | 0.8 | 0.8 | 0.9 | 0.9 | 1.0 | 0.9 | 1.1 | 1.1 |
| S2 | 2.3 | 2.3 | 2.6 | 1.7 | 2.1 | 1.5 | 1.6 | 1.5 | 1.7 | 1.9 | 1.9 | 2.0 | 1.4 | 1.6 | 1.5 |
| S3 | 2.3 | 2.1 | 2.0 | 1.4 | 1.4 | 2.1 | 1.9 | 2.0 | 2.2 | 2.3 | 1.3 | 1.0 | 1.3 | 1.0 | 1.0 |
| S4 | 4.0 | 3.1 | 1.8 | 2.0 | 2.6 | 2.4 | 2.3 | 2.4 | 2.4 | 1.8 | 2.1 | 2.4 | 2.1 | 2.3 | 2.2 |
| S5 | 6.5 | 7.1 | 9.0 | 5.6 | 2.3 | 2.8 | 3.0 | 3.0 | 3.1 | 3.7 | 3.2 | 3.5 | 3.5 | 4.0 | 3.5 |
| Ave. | 3.5 | 3.3 | 3.5 | 2.3 | 2.0 | 2.0 | 2.0 | 1.9 | 2.1 | 2.1 | 1.9 | 2.0 | 1.8 | 2.0 | 1.9 |

The units are in %

FIG.31

Analysis condition and background equivalent concentration (BEC) for all analytes measured with QQQ-ICP-MS.

| Isotope | Mass Shift Q1 | Mass Shift Q2 | Cell Gas Mode | Product ion | BEC (pg/g) |
|---|---|---|---|---|---|
| $^7$Li | 7 | 7 | No Gas | Li$^+$ | 2.3 |
| $^9$Be | 9 | 9 | No Gas | Be$^+$ | 0.2 |
| $^{11}$B | 11 | 11 | He | B$^+$ | 340 |
| $^{23}$Na | 23 | 23 | He | Na$^+$ | 1908 |
| $^{24}$Mg | 24 | 24 | He | Mg$^+$ | 85.5 |
| $^{27}$Al | 27 | 27 | He | Al$^+$ | 327 |
| $^{28}$Si | 28 | 28 | H$_2$ | Si$^+$ | 9011 |
| $^{31}$P | 31 | 47 | O$_2$ | PO$^+$ | 171 |
| $^{32}$S | 32 | 48 | O$_2$ | SO$^+$ | 6395 |
| $^{39}$K | 39 | 39 | H$_2$ | K$^+$ | 2461 |
| $^{40}$Ca | 40 | 40 | H$_2$ | Ca$^+$ | 2184 |
| $^{45}$Sc | 45 | 61 | O$_2$ | ScO$^+$ | 0.9 |
| $^{47}$Ti | 47 | 63 | O$_2$ | TiO$^+$ | 2.9 |
| $^{51}$V | 51 | 67 | O$_2$ | VO$^+$ | 6.6 |
| $^{52}$Cr | 52 | 68 | O$_2$ | CrO$^+$ | 428 |
| $^{55}$Mn | 55 | 55 | He | Mn$^+$ | 6.1 |
| $^{56}$Fe | 56 | 56 | H$_2$ | Fe$^+$ | 229 |
| $^{59}$Co | 59 | 59 | He | Co$^+$ | 0.8 |
| $^{60}$Ni | 60 | 60 | He | Ni$^+$ | 29.6 |
| $^{63}$Cu | 63 | 63 | He | Cu$^+$ | 20.0 |
| $^{66}$Zn | 66 | 66 | He | Zn$^+$ | 60.0 |
| $^{71}$Ga | 71 | 71 | He | Ga$^+$ | 1.5 |
| $^{72}$Ge | 72 | 72 | He | Ge$^+$ | 1.0 |
| $^{75}$As | 75 | 91 | O$_2$ | AsO$^+$ | 5.1 |
| $^{78}$Se | 78 | 94 | O$_2$ | SeO$^+$ | 8.6 |
| $^{85}$Rb | 85 | 85 | He | Rb$^+$ | 2.4 |
| $^{88}$Sr | 88 | 88 | He | Sr$^+$ | 1.1 |
| $^{89}$Y | 89 | 105 | O$_2$ | YO$^+$ | 0.1 |
| $^{90}$Zr | 90 | 106 | O$_2$ | ZrO$^+$ | 0.5 |
| $^{93}$Nb | 93 | 125 | O$_2$ | NbO$_2^+$ | 7.0 |
| $^{95}$Mo | 95 | 127 | O$_2$ | MoO$_2^+$ | 9.4 |
| $^{107}$Ag | 107 | 107 | He | Ag$^+$ | 1.1 |
| $^{111}$Cd | 111 | 111 | O$_2$ | Cd$^+$ | 0.5 |
| $^{118}$Sn | 118 | 118 | H$_2$ | Sn$^+$ | 18.4 |
| $^{121}$Sb | 121 | 121 | He | Sb$^+$ | 0.3 |
| $^{133}$Cs | 133 | 133 | He | Cs$^+$ | 0.8 |
| $^{137}$Ba | 137 | 153 | O$_2$ | BaO$^+$ | 2.0 |

The units are in %

FIG. 32A

Analysis condition and background equivalent concentration (BEC) for all analytes measured with QQQ-ICP-MS.

| Isotope | Mass Shift Q1 | Mass Shift Q2 | Cell Gas Mode | Product ion | BEC (pg/g) |
|---|---|---|---|---|---|
| $^{139}$La | 139 | 155 | $O_2$ | $LaO^+$ | 0.1 |
| $^{140}$Ce | 140 | 156 | $O_2$ | $CeO^+$ | 0.2 |
| $^{141}$Pr | 141 | 157 | $O_2$ | $PrO^+$ | 0.04 |
| $^{146}$Nd | 146 | 162 | $O_2$ | $NdO^+$ | 0.00 |
| $^{147}$Sm | 147 | 163 | $O_2$ | $SmO^+$ | 0.04 |
| $^{153}$Eu | 153 | 169 | $O_2$ | $EuO^+$ | 0.09 |
| $^{157}$Gd | 157 | 173 | $O_2$ | $GdO^+$ | 0.00 |
| $^{159}$Tb | 159 | 175 | $O_2$ | $TbO^+$ | 0.00 |
| $^{163}$Dy | 163 | 179 | $O_2$ | $DyO^+$ | 0.00 |
| $^{165}$Ho | 165 | 181 | $O_2$ | $HoO^+$ | 0.02 |
| $^{166}$Er | 166 | 182 | $O_2$ | $ErO^+$ | 0.03 |
| $^{169}$Tm | 169 | 185 | $O_2$ | $TmO^+$ | 0.01 |
| $^{172}$Yb | 172 | 188 | $O_2$ | $YbO^+$ | 0.00 |
| $^{175}$Lu | 175 | 191 | $O_2$ | $LuO^+$ | 0.02 |
| $^{178}$Hf | 178 | 194 | $O_2$ | $HfO^+$ | 0.2 |
| $^{181}$Ta | 181 | 213 | $O_2$ | $TaO_2^+$ | 1.2 |
| $^{182}$W | 182 | 214 | $O_2$ | $WO_2^+$ | 16.3 |
| $^{205}$Tl | 205 | 205 | No Gas | $Tl^+$ | 0.8 |
| $^{208}$Pb | 208 | 208 | No Gas | $Pb^+$ | 4.6 |
| $^{232}$Th | 232 | 232 | No Gas | $Th^+$ | 0.6 |
| $^{238}$U | 238 | 238 | No Gas | $U^+$ | 0.02 |

The units are in %

FIG. 32B

METHOD OF GEOCHEMICAL CHARACTERIZATION, PRODUCTION ALLOCATION, AND MONITORING USING TRACE AND ULTRA-TRACE ELEMENT ANALYSIS

CROSS-REFERENCE TO RELATED APPLICATION

This application claims the benefit of and priority to U.S. Provisional Patent Application Ser. No. 62/949,311, filed on Dec. 17, 2019, the entire contents of which are incorporated by reference herein.

TECHNICAL FIELD

The disclosure relates generally to the geochemical characterization of a sample. The disclosure relates specifically to the characterization and allocation of crude oil via trace element analysis.

BACKGROUND

Traditional and widely used production allocations methods in the petroleum industry involve flow metering and down-hole flow measurements (MPLT, Memory Production Logging Tests). Production allocation generally refers to the practice of breaking down measures of quantities of extracted hydrocarbons across various contributing sources. The allocation can typically aid with production management and the attribution for taxation and ownership of hydrocarbons for each contributing element that may have unique ownership (from subsurface producing zones, individual wells, leases, or fields) in commingled flows or to storage of petroleum. In unconventional or multi-zone reservoir sources, the attribution may involve monitoring contributions from different parts of the subsurface stratigraphy. In some states in the United States, operators may report a monthly or yearly volume for a group of wells. It is commonly beneficial or required by law to know how each well produces, but often only a single volume for a group of wells or lease is reported. In these cases, the production is unallocated to each of the wells or subsurface units, which are points of concern for production geoscientists and engineers. Without periodic expensive well logging tests and/or flow meter installations and calibrations, there is typically a lack of basis for allocation from the field or lease-level volumes to "by well" volumes. Possible levels of compulsory unitization reporting required by owners or states include subsurface zones, well completions, field units, leases, or transporter pick up points. Crude oil wells may be required to be tested only once per year, although allocation results are more accurate and useful with higher frequency multiple tests of each well per year. This is because allocation from each well or unit within a field can change over the course of a year, and wells in a field or lease can change status or be shut-in. New results from well tests in leases sampled only once per year commonly result not only in reallocation going forward in time but require less certain reallocations going back in time.

Thus, developments in the geochemical characterization of hydrocarbons are needed.

SUMMARY

Aspects of the present disclosure are described in detail with reference to the drawings wherein like reference numerals identify similar or identical elements.

An aspect of the present disclosure provides a system for geochemical characterization of a sample. The system includes a closed reaction chamber configured to perform a high temperature and high-pressure acid digestion test on the sample, a spectrometry system configured to perform trace element analysis on the sample, and a controller. The controller includes a processor and a memory. The memory includes instructions stored thereon, which, when executed by the processor, cause the system to mineralize the sample based on a microwave process using the closed reaction chamber, and perform trace element analysis on the sample by the spectrometry system.

In another aspect of the disclosure, mineralizing the sample may include performing an acid digestion test at a predetermined temperature and a predetermined pressure.

In a further aspect of the disclosure, the trace element analysis may include performing inductively coupled plasma-optical emission spectrometry (ICP-OES) to analyze for major and minor elements.

In an aspect of the present disclosure, the trace element analysis may further include performing inductively coupled plasma-mass spectrometry (ICP-MS) to analyze for low-abundance trace elements.

In another aspect of the present disclosure, the sample may include a hydrocarbon, a food-grade oil, and/or subsurface rock.

In yet another aspect of the present disclosure, the instructions, when executed by the processor, may further cause the system to monitor a well for at least one of a decline or a downhole blockage during production operations based on the trace element analysis of the hydrocarbon sample.

In a further aspect of the present disclosure, the instructions, when executed by the processor, may further cause the system to correlate the sample to a second sample based on the trace element analysis and determine a country origin, oil field origin, and/or source rock origin of the sample of the hydrocarbon sample.

In yet a further aspect of the present disclosure, prior to performing the trace element analysis, the instructions, when executed by the processor, may further cause the system to dry the sample, re-dissolve the digested sample, and dilute the sample.

In yet a further aspect of the present disclosure, the instructions, when executed by the processor, may further cause the system to determine a unique fingerprint based on the trace element analysis of the sample and display, on a display, the unique fingerprint.

An aspect of the present disclosure provides a computer-implemented method for geochemical characterization of a sample, the method including controlling a system including a closed reaction chamber configured to perform a high temperature and high-pressure acid digestion test on the sample, and a spectrometry system configured for performing trace element analysis on the sample. The method further includes mineralizing the sample via a microwave process, and performing trace element analysis via inductively coupled plasma mass spectrometry.

In yet a further aspect of the present disclosure, the sample may include a hydrocarbon, a food-grade oil, and/or subsurface rock.

In yet a further aspect of the present disclosure, mineralizing the sample may be based on a microwave process using a closed reaction chamber configured to perform a high temperature and high-pressure acid digestion test.

In another aspect of the present disclosure, mineralizing the sample may include performing an acid digestion test at a predetermined temperature and a predetermined pressure.

In yet another aspect of the present disclosure, the trace element analysis may be performed by a triple-quadrupole mass spectrometry (TQMS) system.

In a further aspect of the present disclosure, the trace element analysis may include performing inductively coupled plasma-optical emission spectrometry (ICP-OES) to analyze for major and minor elements.

In yet a further aspect of the present disclosure, the trace element analysis may further include performing inductively coupled plasma-mass spectrometry (ICP-MS) to analyze for low-abundance trace elements.

In an aspect of the present disclosure, the method may further include determining a unique fingerprint based on the trace element analysis of the sample and displaying, on a display, the unique fingerprint.

In yet another aspect of the present disclosure, the method may further include, prior to performing the trace element analysis drying the sample, re-dissolving the digested sample, and diluting the sample.

In yet another aspect of the present disclosure, the method may further include correlating the sample to a second sample based on the trace element analysis and determining at least one of a country origin, oil field origin, or source rock origin of the hydrocarbon sample.

In accordance with aspects of the disclosure, a non-transitory computer-readable storage medium in which is stored a program for causing a computer to execute a computer-implemented method for geochemical characterization of a sample is presented. The method includes mineralizing a sample via a microwave process and perform trace element analysis via inductively coupled plasma mass spectrometry.

BRIEF DESCRIPTION OF THE DRAWINGS

A better understanding of the features and advantages of the disclosed technology will be obtained by reference to the following detailed description that sets forth illustrative aspects, in which the principles of the technology are utilized, and the accompanying drawings of which:

FIG. 19 is a table depicting analytical results of the selected twenty analytes in accordance with the present disclosure;

FIG. 20 is a table depicting output contribution fractions (allocation) of the five end-member oils (S1-S5) calculated using different numbers of analytes beyond the minimum of 1-5 (i.e., selected analytes 6-20) in accordance with the present disclosure;

FIG. 21 is a table depicting calculation accuracies of the five end-member oils using different numbers out of the selected analytes (6-20) (sorted from the lowest average ERSD to the highest average ERSD) in accordance with the present disclosure;

FIG. 22 is a table depicting calculation uncertainties of the five end-member oils using different numbers of analytes for the calculation out of the selected 20 analytes (sorted from the lowest average ERSD to the highest average ERSD) in accordance with the present disclosure;

FIG. 23 is a table depicting output contribution fractions (allocations) of the five end-member oils using different number analytes beyond the minimum number of 5 when sorting of the 20 selected analytes is inverted from the highest average ERSD to the lowest average ERSD in accordance with the present disclosure;

FIG. 24 is a table depicting calculation accuracies of the five end-member oils using different number analytes (6-20) beyond the minimum of 5 out of the 20 sorted analytes (sorted form the highest average ERSD to the lowest ERSD) in accordance with the present disclosure;

FIG. 25 is a table depicting calculation uncertainties of the five end-member oils using different numbers (6-20) out of the selected 20 sorted from the highest average ERSD to the lowest average ERSD in accordance with the present disclosure;

FIG. 26 is a table depicting output contribution fractions of the five end-member oils using different numbers (6-20) out of the selected 20 sorted analytes that are sorted by variability from the highest $RSD_V$ to the lowest average $RSD_V$ in accordance with the present disclosure;

FIG. 27 is a table depicting calculation accuracies of the five end-member oils using different numbers (6-20) of the selected 20 sorted analytes from the highest average $RSD_V$ to the lowest average $RSD_V$ in accordance with the present disclosure;

FIG. 28 is a table depicting calculation uncertainties of the five end-member oils using different numbers out of the selected 20 analytes (sorted from the highest average $RSD_V$ to the lowest average $RSD_V$ in accordance with the present disclosure;

FIG. 29 is a table depicting output contribution fractions of the five end-member oils using different numbers (6-20) in accordance with the present disclosure;

FIG. 30 is a table depicting the calculation accuracies of the five end-member oils using different numbers (6-20) out of the selected 20 analytes sorted from the highest $RSD_V$ to the lowest average $RSD_V$ in accordance with the present disclosure;

FIG. 31 is a table depicting calculation uncertainties of the five end-member oils using different numbers (6-20) out of the selected 20 sorted from the lowest average ERSD to the highest average ERSD in accordance with the present disclosure; and FIGS. 32A and 32B are tables depicting analysis conditions and background equivalent concentration (BEC) for all analytes measured with triple-quadrupole mass spectrometry in accordance with the present disclosure.

DETAILED DESCRIPTION

Figure 1A:
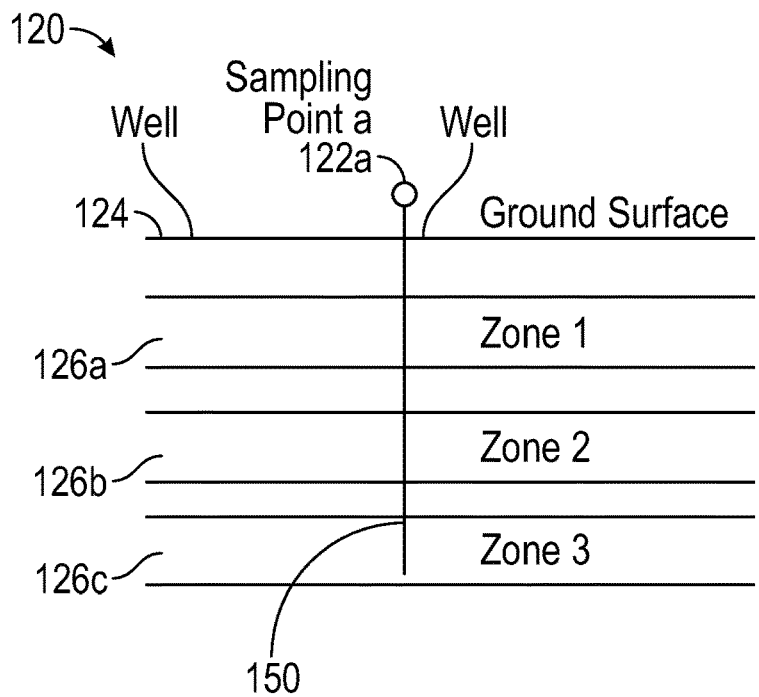
FIGS. 1A and 1B are diagrams of oil fields and oil wells.

This disclosure relates to geochemical characterization of hydrocarbons. More specifically, the present disclosure relates to the identification and quantification of single compounds in hydrocarbons. Although the present disclosure will be described in terms of specific aspects, it will be readily apparent to those skilled in this art that various modifications, rearrangements, and substitutions may be made without departing from the spirit of the present disclosure. The scope of the present disclosure is defined by the claims appended hereto.

For purposes of promoting an understanding of the principles of the present disclosure, reference will now be made to exemplary aspects illustrated in the drawings, and specific language will be used to describe the same. It will nevertheless be understood that no limitation of the scope of the present disclosure is thereby intended. Any alterations and further modifications of the inventive features illustrated herein, and any additional applications of the principles of the present disclosure as illustrated herein, which would occur to one skilled in the relevant art and having possession of this disclosure, are to be considered within the scope of the present disclosure.

Mineralization refers to a procedure that eliminates the organic structure of the oil by acid digestion (i.e., oxidization), or combustion, so that the organic samples can be introduced into the analytical instrument in aqueous form. If complete or nearly complete, this can remove or minimize the spectral and polyatomic interferences caused by the complex organic matrix in crude oils, and avoid carbon deposition, which may clog the sampler or skimmer cones of the inductively coupled plasma-mass spectrometry (ICP-MS) and can cause plasma instability or even extinction. In addition, aqueous sample solutions enable the use of inexpensive aqueous standards for external calibration.

Figure 1B:
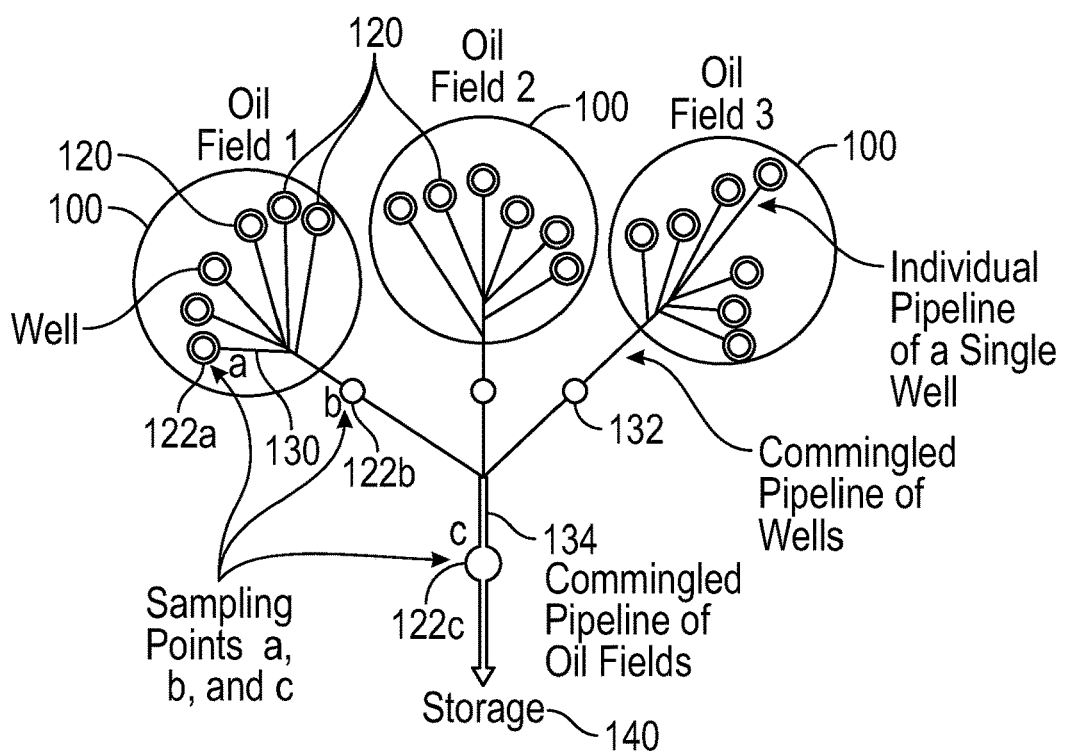

Referring to FIGS. 1A and 1B, oil fields and oil wells are shown. An oil field 100 generally includes a number of wells 110 and individual pipelines 130 for the individual well(s) 100. The individual pipelines 130 are configured to convey the oil from the individual well(s) 100 to a commingled pipeline of wells 132. The commingled pipeline of wells 132 is configured to convey the oil to a commingled pipeline of oil fields 134 (e.g., oil fields 1, 2, and 3) for storage 140. Oil may be sampled for example, at various sampling sites "A" 122a, "B" 122b, and "C" 122c. Sampling site "A" 122a may be at a well 110 above the ground surface 124.

Figure 2:
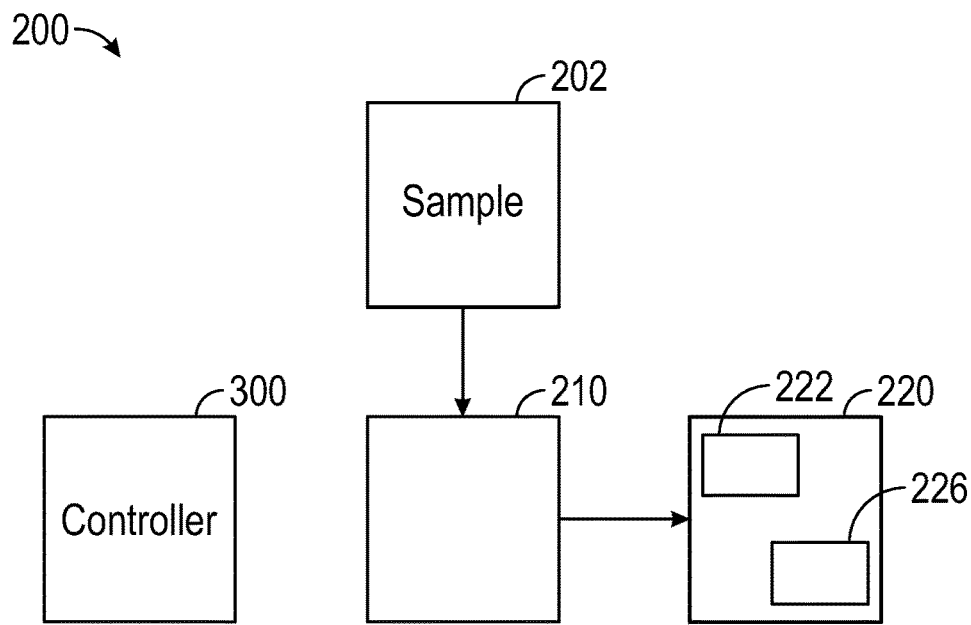
FIG. 2 is a block diagram of a system for geochemical characterization of hydrocarbons in accordance with aspects of the disclosure.

Referring now to FIG. 2 a block diagram of a system for geochemical characterization of hydrocarbons is shown. The system 200 generally includes a closed reaction chamber 210 configured to perform a high temperature (e.g., about 90° C.), and high-pressure (e.g., about 19.9 MPa,) acid digestion test, a spectrometry system 220 configured for analyzing for elements, and a controller 300.

The spectrometry system 220 generally includes an ICP-OES system 222 configured for analyzing for major and minor elements by inductively coupled plasma-optical emission spectrometry (ICP-OES) using and a triple-quadrupole mass spectrometry (TQMS) system 226 configured for analyzing for low-abundance trace elements by inductively coupled plasma-mass spectrometry (ICP-MS).

ICP-OES 222 is a technique used for the detection of chemical elements. It is a type of emission spectroscopy that uses the inductively coupled plasma to produce excited atoms and ions that emit electromagnetic radiation at wavelengths characteristic of a particular element. In aspects, the plasma may be a high temperature source of ionized source gas (for example, often argon). The plasma may be sustained and maintained by inductive coupling from cooled electrical coils generally at megahertz frequencies. The source temperature may be in the range from about 6000 deg. K to about 10,000 deg. K. The intensity of the emissions from various wavelengths of light are proportional to the concentrations of the elements within the sample.

A TQMS system 220 is generally a tandem mass spectrometer consisting of two quadrupole mass analyzers in series, with a (non-mass-resolving) radio frequency (RF)-only quadrupole between them to act as a cell for collision-induced dissociation.

The disclosed technology includes a method of geochemical trace and ultra-trace elements fingerprinting of crude oils (unmixed or commingled) and then allocating or unmixing of commingle crude oils derived from two or more sources that can be commingled from about two to about seven producing zones in a subsurface well, from commingled oils from between about two to about seven wells in an oil field pipeline, or commingled crude oils from several pipeline streams where pipelines merge. The methods include geochemical allocation using trace and ultra-trace elemental abundance data and differs from organic molecular techniques or PMT well logging techniques that tend to be more costly. The geochemical fingerprinting technique can also be used to monitor wells for decline and downhole blockage or other problems during production operations. The fingerprinting also enables "oil to oil" and "oil to source rock" correlations that can be used to determine the country origin, oil field origin, and/or source rock origin of the crude oils for exploration, production, or national security reasons. Although petroleum (e.g., oil) and the petroleum industry is used as example to illustrate the disclosed technology, it is contemplated the disclosed technology is suitable for other industries and products as well. For example, the disclosed technology is suitable for the food industry (e.g., food grade oils, such as vegetable oil, and/or oil derived from animal fat) or to subsurface rock to mix unmatched oils.

Thus, the disclosed technology streamlines multi-element analysis for a more complete fingerprinting of oils by using a single-reaction-chamber microwave digestion sample preparation method and then analyzing for major and minor elements by ICP-OES using the ICP-OES system 222 and low-abundance trace elements by ICP-MS with a TQMS 226 system. Results to date using this approach have shown that complete elemental recovery and removal of organic matrices can be achieved safely and that up to about 57 elements can be determined in oils with good accuracy and precision. The removal of organic matrices during digestion not only helps to limit the formation of polyatomic spectral interferences but improves instrument stability and reduces carbon buildup in the sample introduction and interface regions, which has traditionally plagued "dilute-and-shoot" methods.

Figure 3:
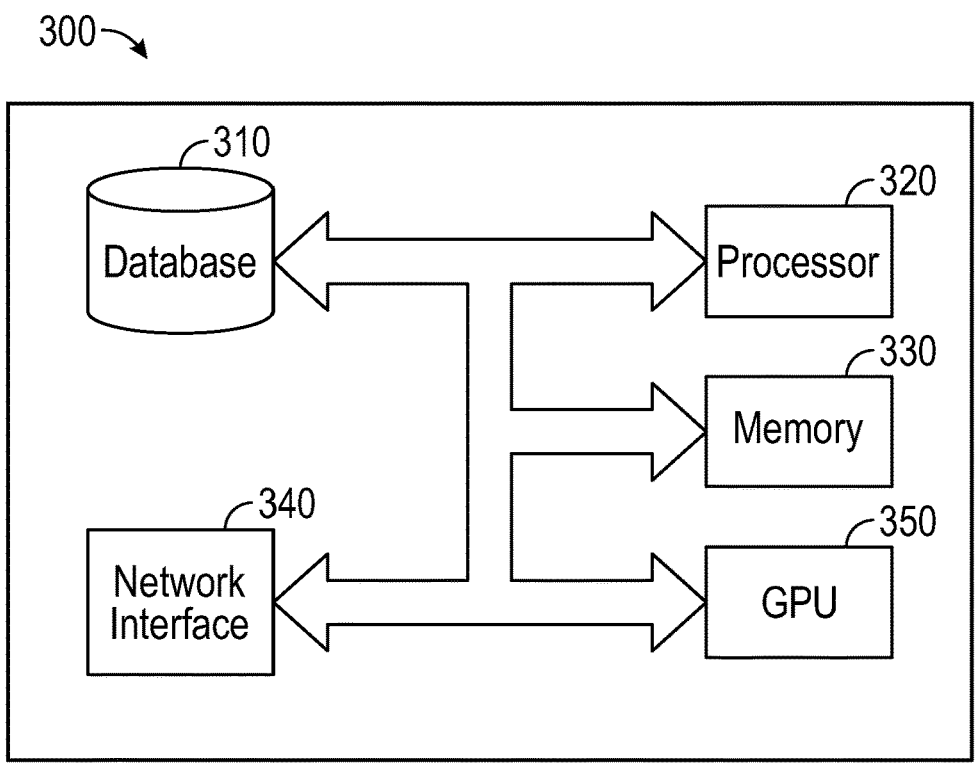
FIG. 3 is a block diagram of an exemplary server of FIG. 2 in accordance with aspects of the present disclosure.

Referring now to FIG. 3, there is shown an illustration of exemplary components in the controller 300 of FIG. 2, in accordance with aspects of the present disclosure. The controller 300 includes, for example, a database 310, one or more processors 320, at least one memory 330, and a network interface 340.

The database 310 can be located in storage. The term "storage" may refer to any device or material from which information may be capable of being accessed or reproduced or held in an electromagnetic or optical form for access by a computer processor. A storage may be, for example, volatile memory such as RAM, non-volatile memory, which permanently hold digital data until purposely erased, such as flash memory, magnetic devices such as hard disk drives, and optical media such as a CD, DVD, Blu-ray disc, or the like.

In various aspects, data may be stored on the controller 300. The data can be stored in the server database 310 and sent via the system bus to the processor 320. As will be described in more detail later herein, the processor 320 executes various processes based on instructions that can be stored in the memory 330 and utilizing the data from the database 310.

Figure 4:
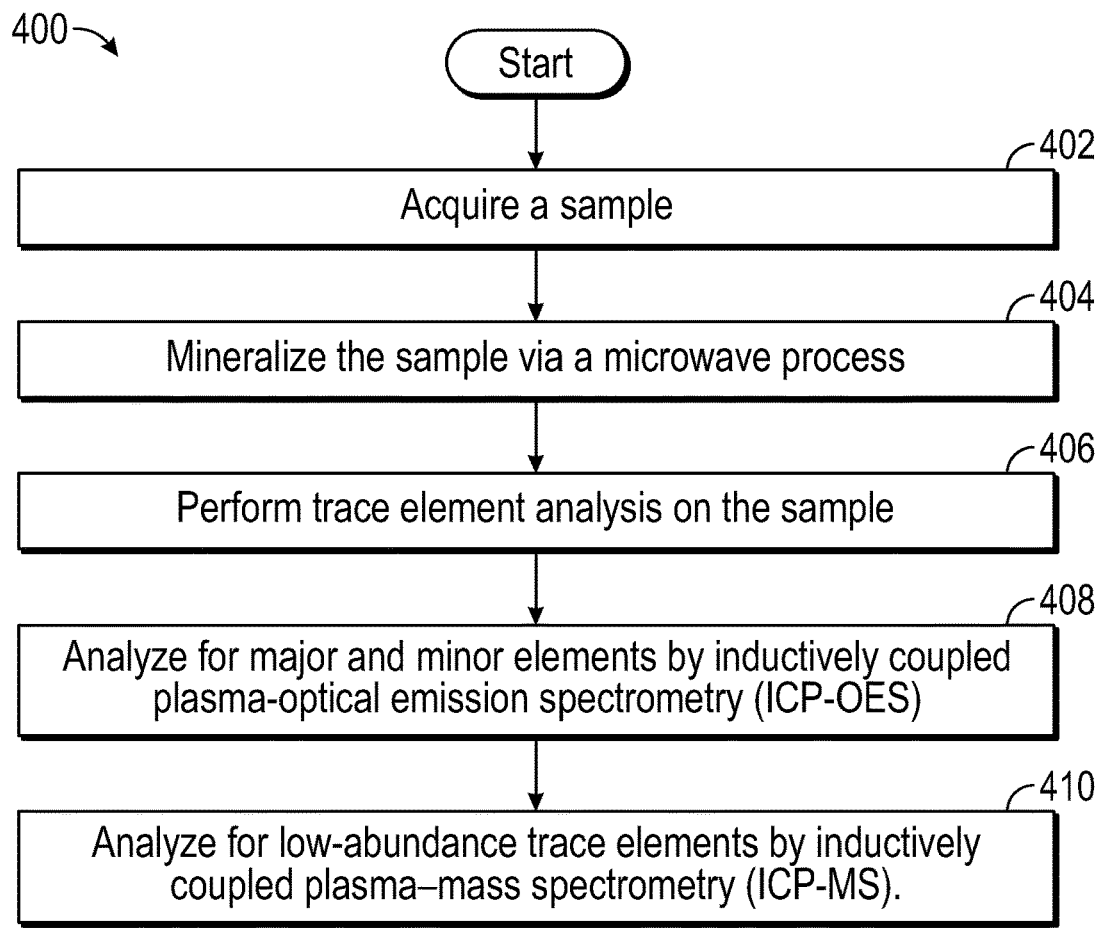
FIG. 4 is a flow diagram for a method for geochemical characterization of a sample in accordance with aspects of the present disclosure.

Referring to FIG. 4, there is shown a flow chart of an exemplary computer-implemented method 300 for geochemical characterization of a sample in accordance with aspects of the present disclosure. In accordance with aspects of the present disclosure, the controller 300 operates to improve or optimize the matching of a user to an event. Although the steps of FIG. 4 are shown in a particular order, the steps need not all be performed in the specified order, and certain steps can be performed in another order. For simplicity, FIG. 4 will be described below, with the controller 300 performing the operations. However, in various aspects, the operations of FIG. 3 may be performed in part by the controller 300 of FIG. 2 and in part by another device, such as a remote server. These variations are contemplated to be within the scope of the present disclosure.

Initially, at step 402, the operation acquires a sample. For example, the sample may include a hydrocarbon, a food-grade oil, and/or subsurface rock.

Next, at step 404, the operation may mineralize the sample via a microwave process. For example, the sample may be mineralized based on a microwave process using a closed reaction chamber. In aspects, mineralizing the sample may be performed by performing an acid digestion test at a predetermined temperature and a predetermined pressure.

For example, a closed reaction chamber 210 (e.g., a Single Reaction Chamber (SRC) Microwave Digestion System), may be used for performing the high temperature, and high-pressure acid digestion test (FIG. 19). The closed reaction chamber 210 (FIG. 2) may be connected to controller 300 (FIG. 2) for monitoring the temperature (T1) and pressure inside the closed reaction chamber 210, and the temperature (T2) of the outer wall of the closed reaction chamber 210. For example, the maximum allowed values of T1, pressure, and T2 may be about 300° C., about 19.9 MPa, and about 90° C., respectively. For example, if T2 reaches 60° C., or digestion pressure reaches 15 MPa, the system may be shut down automatically. For example, the maximum T2 and digestion pressure may be are 43° C. and 10.5 MPa, respectively. For the digestion test, about 15 ml and about 40 ml quartz and Teflon (PTFE) digestion tubes may be used. There may be a small lateral hole on the Teflon lid of the tube, so the inner space is connected to the outside sealed pressure chamber to keep pressure balance. For example, in one run, up to about fifteen 15 ml tubes, or about five 40 ml tubes can be loaded for digestion depending on sample size desired. The closed reaction chamber 210 may be coupled with a PTFE liner, which is used to hold the base load. For example, the base load may consist of 130 ml of Milli-Q water+5 ml of 16 N $HNO_3$. The base load absorbs the microwave energy to heat the sample. Pure $N_2$ may be filled into the PTFE liner to provide initial high pressure and make an inert environment for the digestion. The initial pre-pressure should be over 4 MPa, and below 4.5 MPa.

In aspects, the operation may dry the sample, re-dissolve the digested sample, and dilute the sample. The sample may be diluted with, for example, with $HNO_3$.

Next, at step 406, the operation performs trace element analysis on the sample. The trace element analysis may be performed by the spectrometry system 220 of FIG. 2. First, at step 408, the operation analyzes the sample for major and minor elements by inductively coupled plasma-optical spectrometry using an ICP-OS system 222 (FIG. 2). Next, at step 410, the operation analyzes the sample for low-abundance trace elements by inductively coupled plasma-mass spectrometry using a TQMS system 226 (FIG. 2).

In aspects, the operation may determine a unique fingerprint based on the trace element analysis of the sample and display, on a display, the unique fingerprint. For example, a sample of a crude oil may have a unique fingerprint, and that fingerprint would be displayed on a display. In aspects, the operation may determine, based on specific target elements in the sample, from which end-member oils the sample came.

Referring to FIGS. 5 to 32 example experimental data is shown. The disclosed geochemical characterization method includes trace elemental analyses on a sample by ICP-OES and ICP-MS used in tandem that has potentially broader applications, lower costs and may be complimentary to other techniques. The relationship between the mass fractions of specific target elements in end-member oils and commingled oils is linear. To test the method, below is presented initial laboratory mixing experiments of five crude oils in known proportions, analyzing the trace elements of the end members and mixtures, and testing of the viability of unmixing the commingled oil into the known proportions for the mixture.

A TQMS system 226 (for example, Agilent Technologies® Model 8800) and an ICP-OES system 222 (for example, Agilent Technologies® Model 725) were used to analyze the concentration of trace elements. The IDL (instrumental detection limit) of the TQMS system 226 can be as low as 0.02 pg/g, commonly around 1 pg/g, and commonly about 2.0 ng/g for ICP-OES. ICP-MS and ICP-OES, therefore, were used for low abundance trace elements determination and high abundance trace elements determination, respectively. Typically, vanadium (V), Nikel (Ni), and sulfur (S) and occasionally others in natural crude oils are high abundance elements, which may need to be determined by the ICP-OES system 222, but the majority of trace elements are in low abundance that need to be determined by the TQMS system 226. Compared to one quadrupole mass filter (Q-ICP-MS), which has a common IDL of around 10 pg/g, the TQMS system 226 is more sensitive and has a lower IDL (around 1 pg/g). Some ultra-trace elements are not detectable for Q-ICP-MS especially when interferences are problematic but can be determined by the TQMS system 226 (e.g., rare earth elements, P, S etc.). The TQMS system 226 is able to remove or minimize polyatomic interferences (e.g., $75As+$ and $40Ar35Cl+$), isobaric interferences (e.g., $40K+$ and $Ar+$), and non-mono-charged interferences (e.g., $78Se+$ and $156Gd2+$), which are the most common interferences in mass spectrometry, while Q-ICP-MS is not. Thus, in order to maximize the number of high and low abundance analytes reported for natural samples, including the NIST RM examined, in aspects the overall method of analysis for crude oil involves utilization of the TQMS system 226 in tandem with the ICP-OES system 222. The operating conditions of the TQMS system 226 and the ICP-OES system 222 are summarized in the table shown in FIG. 19. 2% (v/v) $HNO_3$ was used as ICP rinsing and carrier solution, and for dilution of calibration standards. The isotope, mass shift, cell gas mode, product ion, and background equivalent concentration (BEC) by the TQMS system 226 are summarized in the table shown in FIG. 32. "Mass shift" mode refers to the interferences removal technique using different m/z settings for Q1 and Q2, while the technique using identical m/z for Q1 and Q2 is called the "on mass" mode. Both "mass shift" and "on mass" are "MS/MS" mode (both Q1 and Q2 are in use), as opposed to the "Single Quad" mode using only Q-ICP-MS. BEC was calculated based on the mean of the blank measurements. Small oscillations exist for IDL and BEC between one analytical run and another, because ICP's sensitivity is not exactly the same from test to test, and even from sample to sample because the argon flow rates, plasma temperature, and chiller working conditions are not always the same.

Presented herein is a multi-element laboratory test and a computational method for trace element production allocation. Results show a precise method of trace element mass fraction measurement by the ICP-OES system 222 and the TCPMS system 226 to achieve multi-element fingerprints of five end-member oils and a commingled oil. Based on determined end-member and commingled oil trace element mass fractions, a successful computational method of unmixing the commingled oils to allocate the proportions of the five end-members in the mixture has been developed. Optimal calculations, accuracies and precision of the allocated proportions are achieved when the most precise replicated analytical measurements of targeted elements are used and when the number of precisely determined analytes in calculations exceed eight. Based on replicates, low precision analytes should be avoided in calculations. Accuracies of most calculations for all the five end-member oil target proportions are within about 4%, and the best can be less than about 0.6% for all end members (average 0.17% and median 0.1%). Most calculation uncertainties in terms of relative standard deviations of the five end-member oils are within 3%, and the best achieved can be less than about 2.3% for all end members (average 1.2% and median 0.9%). The trace element allocation method proposed can significantly lower cost compared with more expensive allocation methods, can be accomplished more frequently because of the significantly lower costs, and therefore present more precise well and field monitoring eliminating the need for back allocation between less frequent monitoring methods. Oil field, collection, and sales point testing of commingled oils will be useful in establishing the trace element allocation method. These tests can be conducted in conjunction with other methods (e.g., molecular geochemical allocation, downhole MPLT allocation, and flow metered allocation methods) to achieve assessment of the method proposed.

Ultra-clean reagents were used for the trace element studies. Water used for cleaning of the experimental Teflon and quartz vessels and dilution of acids and samples was first purified by a water purification system (not shown), and then further purified by a water polishing system (not shown). Concentrated hydrochloric acid and concentrated nitric acid used for digestions or dilutions in this investigation were doubly-distilled in a sub-boiling distillation system. A solution of about 30% hydrogen peroxide about was also utilized for oil digestion. The calibration standards utilized throughout this investigation were aqueous multi-element standards made from two 10 µg/ml multi-element ICP standards. Five black intermediate natural crude oils (S1, S2, S3, S4, and S5) from the Chevron-Texaco® oil library at the University of Houston were used as end-member oils to prepare the commingled oils for allocation test.

Figure 5:
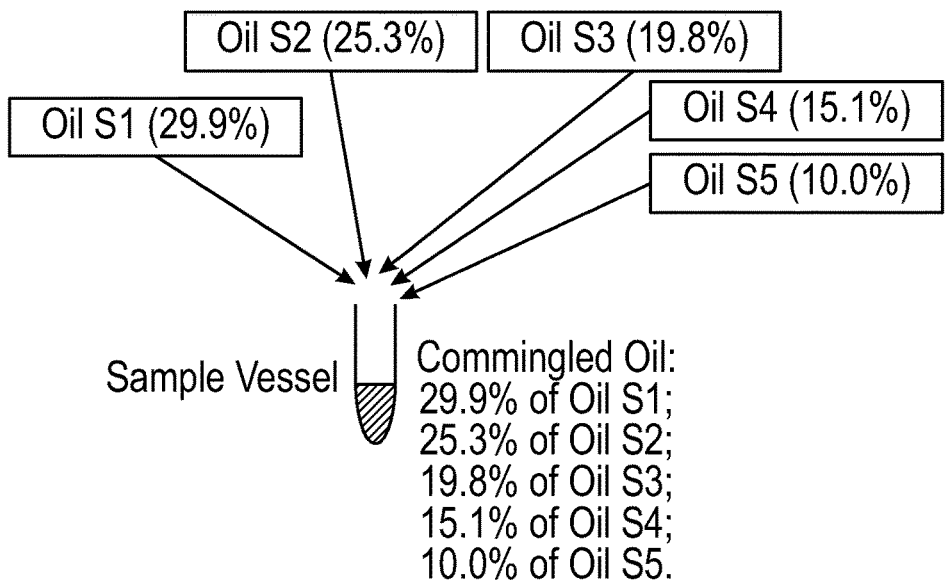
FIG. 5 is a diagram depicting the comingling of five different oils in accordance with the present disclosure.
Figure 6:
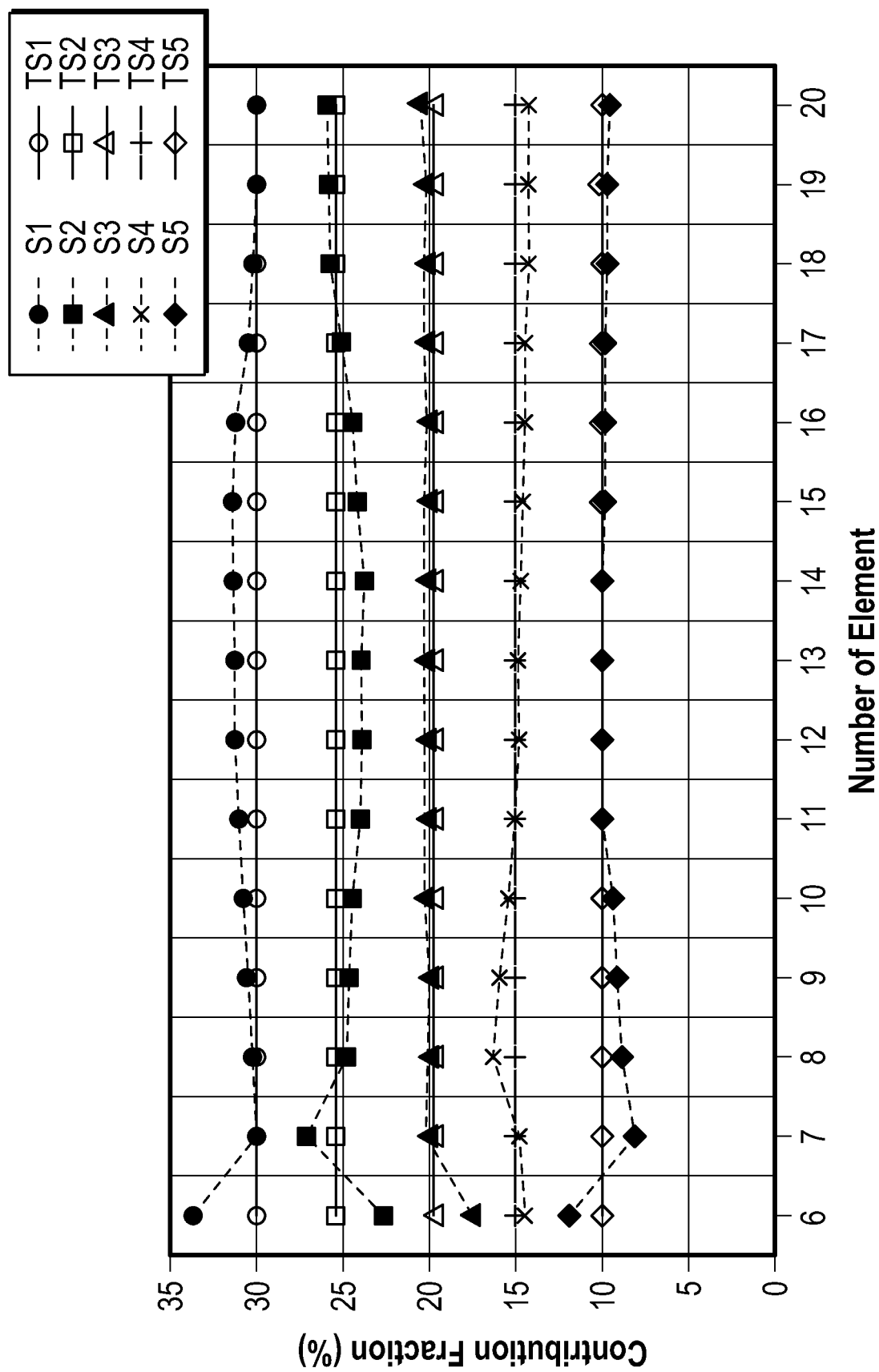
FIG. 6 is a graph depicting contribution fractions for different numbers of analytes for an experimental relative standard deviation (ERSD) Sort 1 (lowest to highest) in accordance with the present disclosure.
Figure 7:
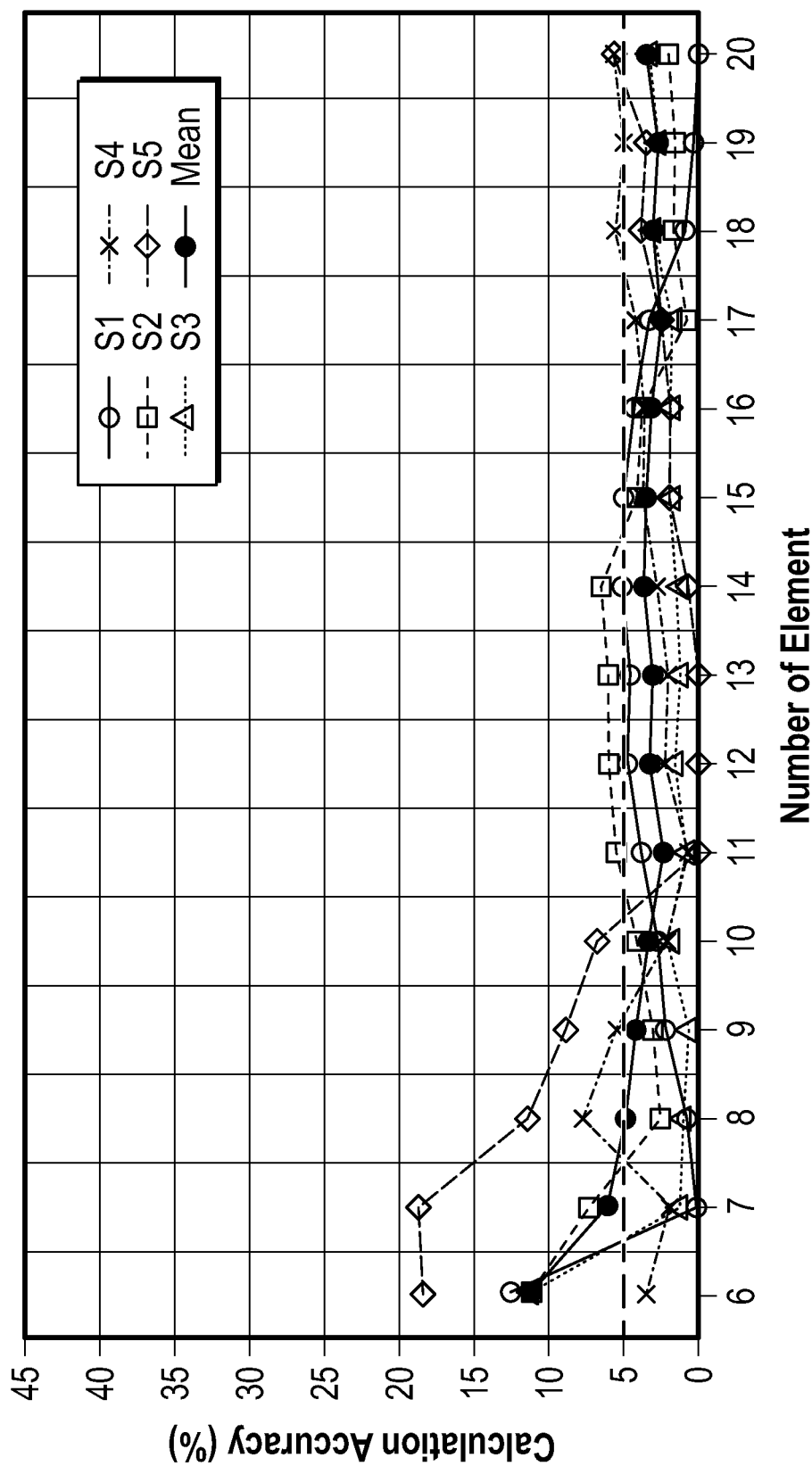
FIG. 7 is a graph depicting calculation accuracies for different numbers of analytes (6-20) for the ERSD Sort 1 in accordance with the present disclosure.
Figure 8:
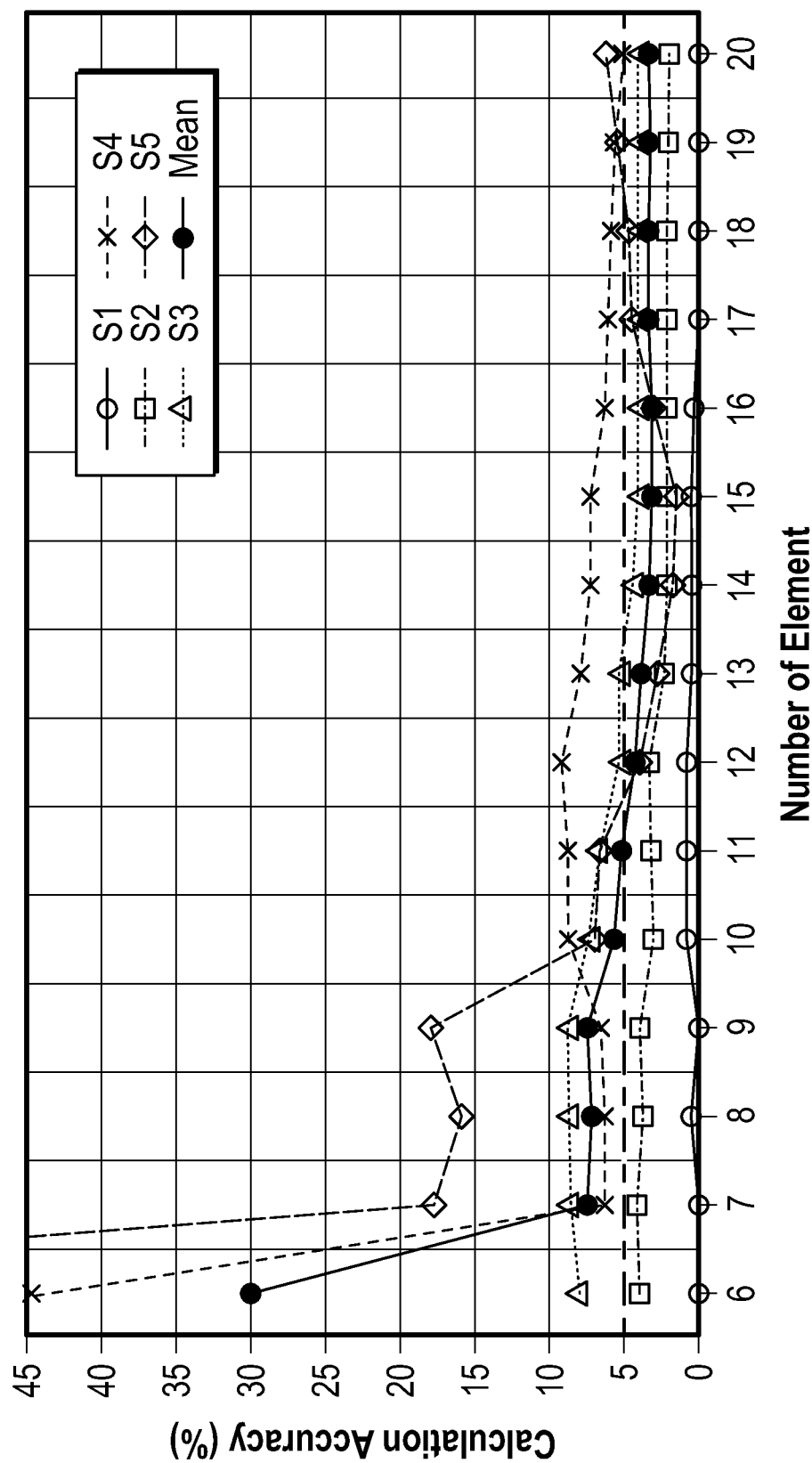
FIG. 8 is a graph depicting calculation accuracies for different numbers of analytes (6-20) for the ERSD Sort 2 (highest to lowest) in accordance with the present disclosure.

At first, the five natural crude oils were mixed artificially to make the commingled oil. To help ensure homogeneity of the five natural crude oil samples (S1-S5), the samples were heated in a water bath at 56° C. for over 10 h and then shaken vigorously prior to mixing. Then at least 1 g of each of the five natural crude oil samples (S1: 3.01 g; S2: 2.55 g; S3: 1.99 g; S4: 1.52 g; S5: 1.01 g) was transferred into a PP (polypropylene) test tube for mixing. A minimum amount of commingled oil (about 10 g) was used for the test to ensure sample homogeneity for the desired accuracy and precision and to have enough made up sample for 3 replicate analyses for trace element analysis. Therefore, the exact contribution fractions by weight of the five natural crude oil samples S1-S5 to the created commingled oil sample are 29.9%, 25.3%, 19.8%, 15.1%, and 10.0%, respectively (FIG. 5). Then the commingled oil was shaken intensively and left overnight in the heated water bath for complete homogeneous mixing. Three sets of samples were prepared for replicate trace element tests to evaluate the method uncertainties for both the end-member oils and commingled oil.

A microwave-assisted mineralization technique with mixed acids under high temperature and high pressure was used for oil digestion. One of skill in the art would be familiar with this technique and how to use it for oil digestion. The microwave used was an SRC Microwave Digestion System. After microwave digestion, drying, re-dissolving, the digested oil samples were further diluted to 9 g with 2% (v/v) $HNO_3$. An aliquot of the digested sample solution was used for the ICP-OES system 222 prescreening determination and quantification of high abundance elements. The remaining solution was used for determination of low abundance elements with the TQMS system 226. For the prescreening analysis with the ICP-OES system 222, 1 g of the sample solution was extracted and further diluted to 6 g. Routinely, 22 elements which may have high abundance in crude oils are screened (Al, As, B, Ba, Ca, Co, Cr, Cu, Fe, K, Mg, Mn, Mo, Na, Ni, P, S, Se, Sr, Ti, V, and Zn) by the ICP-OES system 222. Lower abundance elements when not quantified on the ICP-OES system 222 can be analyzed for up to 57 elements by the TQMS system 226.

A MATLAB® program called "ALLO-TRACE" was developed and used to calculate the relative contributions of the end-member oils (samples S1-S5) to the commingled oils. The input of geochemical data are the determined mass fractions of certain target elements in both end-member oils and commingled oils. The output data (results) are the contribution fractions of the mechanically mixed end-member oils (samples S1-S5) to the commingled oils and the SDs (standard deviations) of the calculations. Similar to the technique based on peak heights in molecular analysis, a linear relationship exists between the mass fractions of certain target elements of the five end-member oils and the mass fractions of corresponding target elements in the commingled oils, which is defined by the following equation:

$$C_{commingled} = F1 \times C1 + F2 \times C2 + F3 \times C3 + F4 \times C4 + F5 \times C5$$

where $C_{commingled}$ refers to the determined mass fraction of a certain target element in the commingled oil. C1, C2, C3, C4, and C5 are the determined mass fractions of this target element in the five end-member oils, respectively. F1, F2, F3, F4, and F5 are the contribution mass fractions or proportions by weight (mass/mass) of the five end-member oils, respectively. The objective of production allocation for this study is to determine member oils F1-F5. There are at least three potential sources of errors: measurement errors in both end-member oils and commingled oils, heterogeneity of the crude oils, and errors related to possible contaminations during sample preparation. These errors could lead to non-linear relationship between the mass fractions of certain target elements of the five end-member oils and the mass fractions of corresponding target elements in the commingled oils. The resulting mass fraction errors of certain target elements may result in wrong or even unreasonable solutions (i.e., negative contribution fractions or unreasonable contribution fractions higher than 100%). To minimize the impact of the possible errors, the ALLO-TRACE program was developed based on a bootstrap (Ntime) in tandem with random selection method (Nrand).

Only those elements that have simultaneous good ERSDs (experimental relative standard deviations) with optimal values of ERSD≤10-20% meeting the acceptability limits for replicates in both end-member oils and the commingled oils were generally selected to calculate the corresponding contribution fractions. According to this criterion, 20 analytes (Na, Mg, S, Ca, Ti, V, Mn, Fe, Co, Ni, Cu, Zn, Ga, Sr, Y, Zr, Mo, Cd, Ba, and Pb) were selected for allocation calculations. Their analyzed averaged mass fractions and the corresponding uncertainties in both the end-member oils and the commingled oils for the three replicate tests are summarized in Table 1.

In order to obtain a set of proportion solutions (mass contribution fractions F1, F2, F3, F4, and F5) for Eq. (1) with five end-member oils, a minimum of five analytes should be used for allocation calculations. Every time the MATLAB® program will select one out of the 20 elements (all six ERSDs≤20%) and substitute the determined mass fractions of this selected element (e.g., Ni) in the five end-member oils and commingled oil into Eq. (1) (Eq. (1)-Ni). Then the program will assign a predefined constant number of sets of proportion solutions (F1, F2, F3, F4, and F5, respectively) randomly to Eq. (1)-Ni. The predefined constant number of sets of proportion solutions is called "Nrand." These assigned contribution fractions are subject to two restrictions: every assigned contribution fraction is between zero and one, and the sum of one set of proportion solutions (F1+F2+F3+F4+F5) for a certain element is equal to one. Then the program will find the set (F1-F5) of proportion solutions (e.g., Set 1) that has the smallest difference between the left side and right side of Eq. (1)-Ni. The calculation program conducts this kind of calculation for predefined multiple times to achieve a number of such sets of proportion solutions (Set 1, Set 2, Set 3, to Set 100, or Set 1000, etc.). The predefined multiple times of calculation is called "Ntime." An analyte can be selected repeatedly and randomly and used multiple times in calculations. Based on this predefined number of solutions, the average F1-F5 in these sets of proportion solutions is calculated and provides the final output contribution fractions for all end members crude oils (S1-S5). The calculation accuracy of a certain end-member oil is given by the following Equation 2:

Calculation accuracy=|(Output contribution fraction/True contribution fraction)×100%−100%| where the True contribution fractions refer to the prepared contribution fractions of the five natural crude oil samples within the commingled oil sample (29.9%, 25.3%, 19.8%, 15.1%, and 10.0%). The calculation uncertainties of the output contribution fractions can be obtained using the calculation SDs (1σ, n=Ntime) of these sets of proportion solutions according to Equation 3:

Calculation uncertainty=(SD/Output contribution fraction)*100%

The number of analytes used in the calculations can be increased beyond 6 by increments of 1 to achieve more precise and accurate solutions. Because many more elements are measured than end members or producing zones, the system of equations is an over-constrained system of equations, and that allows refinements of various solutions using a number of optimization techniques described below.

Summarized in FIG. 20, "mass shift" mode refers to the interferences removal technique using different m/z settings for Q1 and Q2, while the technique using identical m/z for Q1 and Q2 is called the "on mass" mode. Both "mass shift" and "on mass" are "MS/NIS" mode (both Q1 and Q2 are in use), as opposed to the "Single Quad" mode using only Q-ICP-MS. BEC was calculated based on the mean of the blank measurements. Small oscillations exist for IDL and BEC between one analytical run and another because ICP's sensitivity is not exactly the same from test to test and even from sample to sample because of the argon flow rates, plasma temperature, and chiller working conditions.

Example 1

Five potential factors that may affect the results (calculation accuracies and calculation uncertainties) were investigated: 1) the number of analytes used for allocation calculation, 2) the ERSDs of the average mass fractions of the selected analytes in both end-member oils and commingled oils for the three replicated tests, 3) the number of sets of proportion solutions that are randomly assigned (Nrand) in a single calculation, 4) the number of times that the calculations are conducted by the program (Ntime), and 5) the variations between the mass fractions of the five end-member oils and commingled oil for a certain element.

Figure 9:
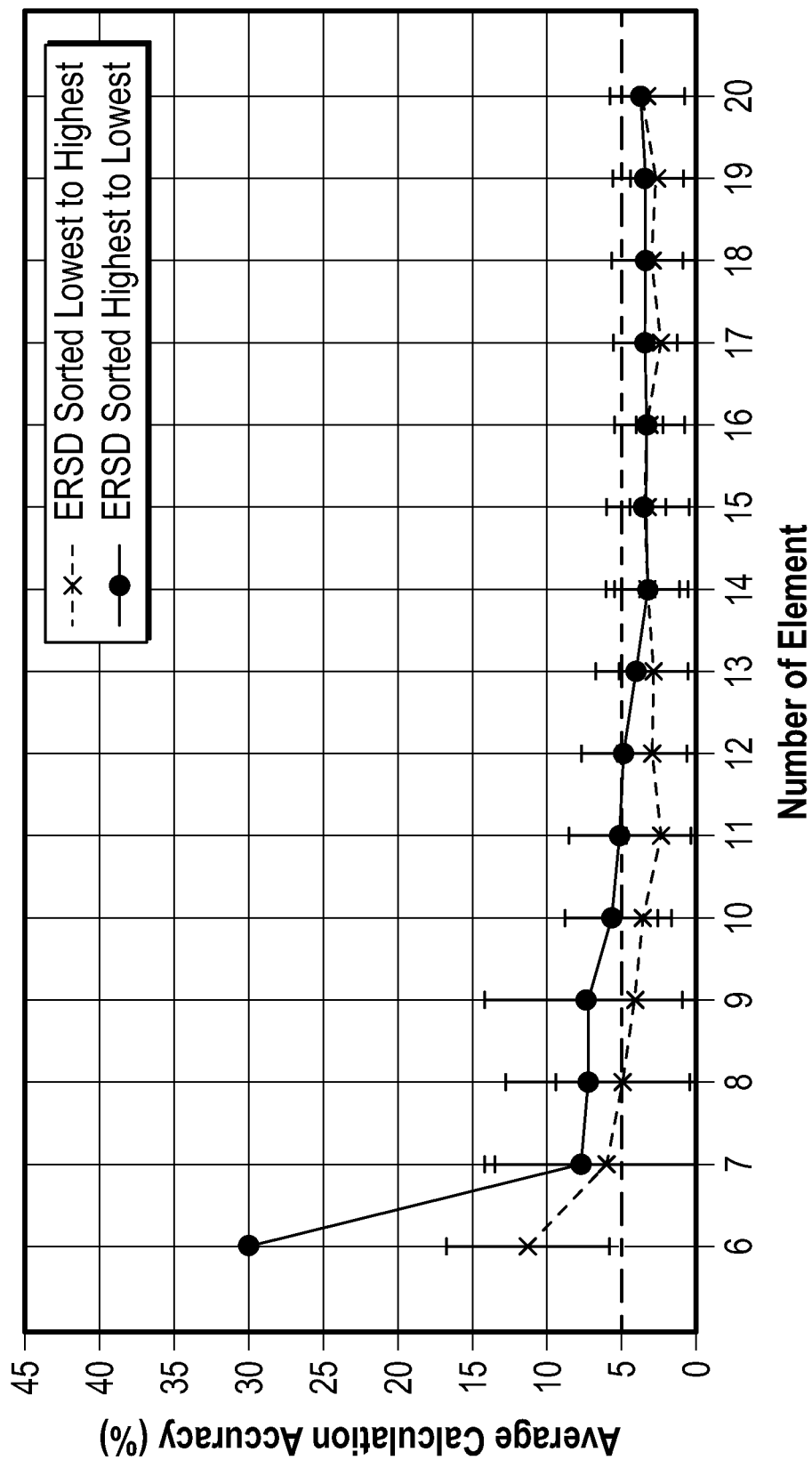
FIG. 9 is a graph depicting average calculation accuracies for different numbers of analytes for both sorting strategies in accordance with the present disclosure.
Figure 10:
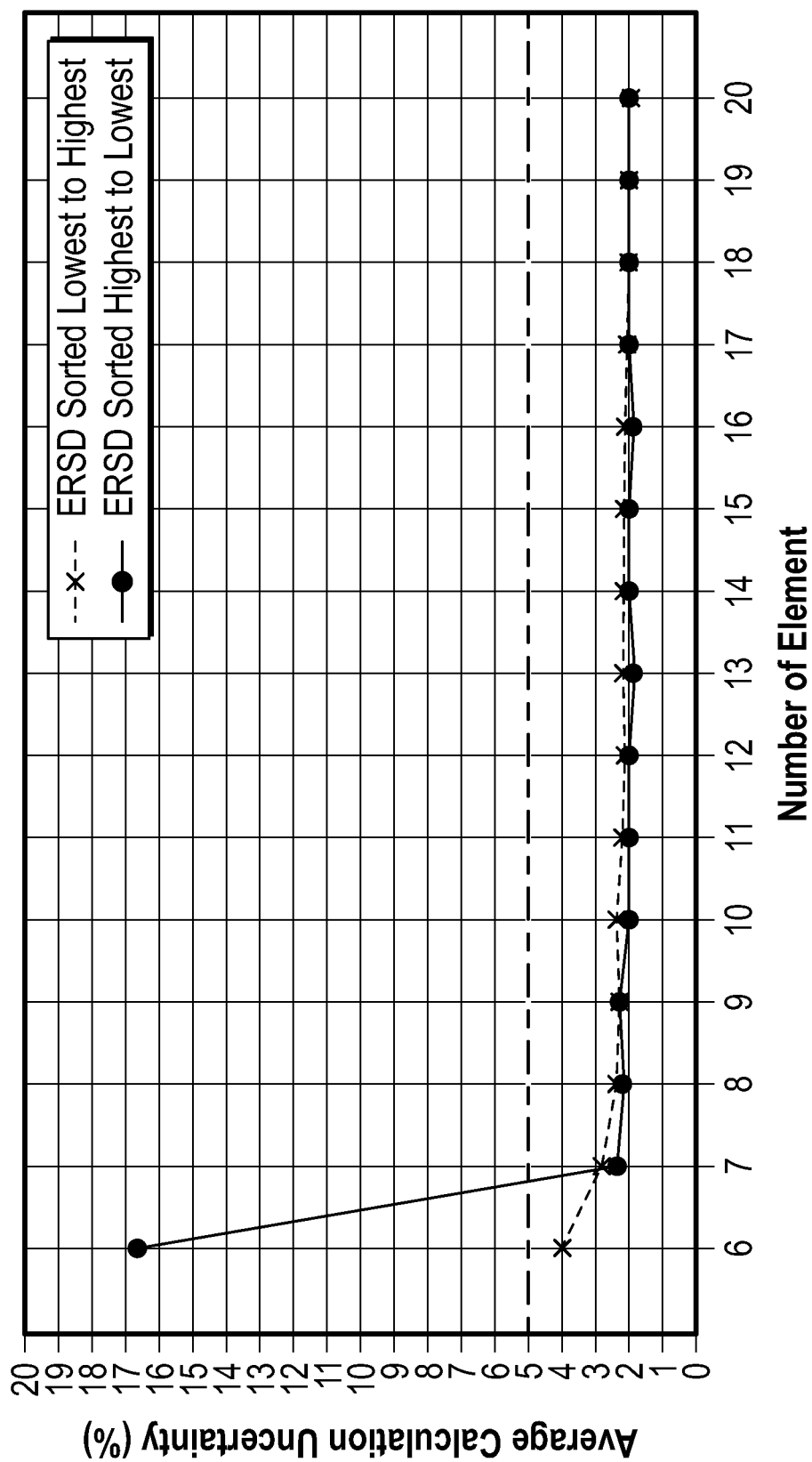
FIG. 10 is a graph depicting average calculation uncertainties for different numbers of analytes (6-20) for both ERSD sorting strategies in accordance with the present disclosure.
Figure 11:
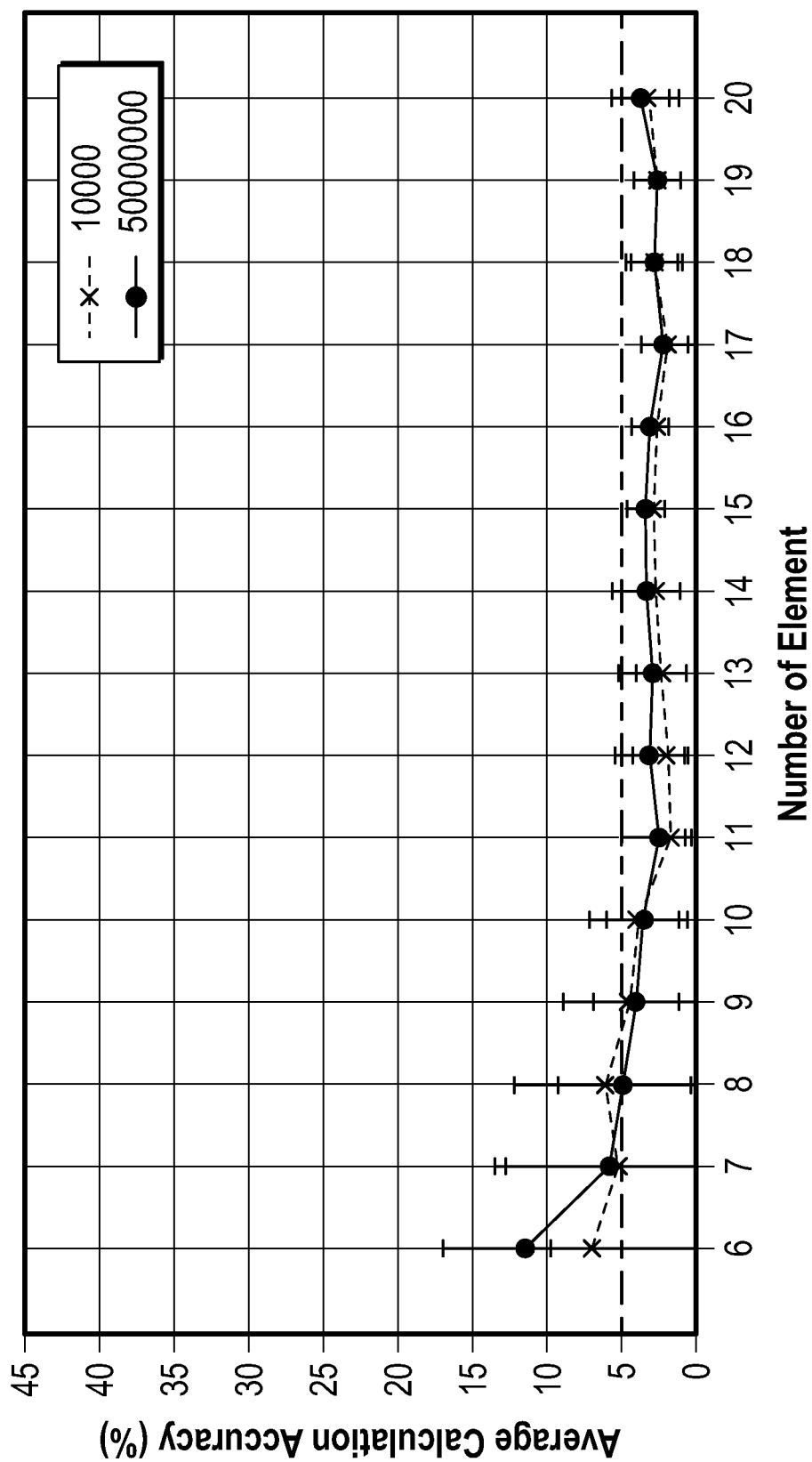
FIG. 11 is a graph depicting average calculation accuracies for different numbers of analytes (6-20) for a constant number of sets of proportion solutions (Nrand)=10,000 and 50,000,000, respectively, in accordance with the present disclosure.
Figure 12:
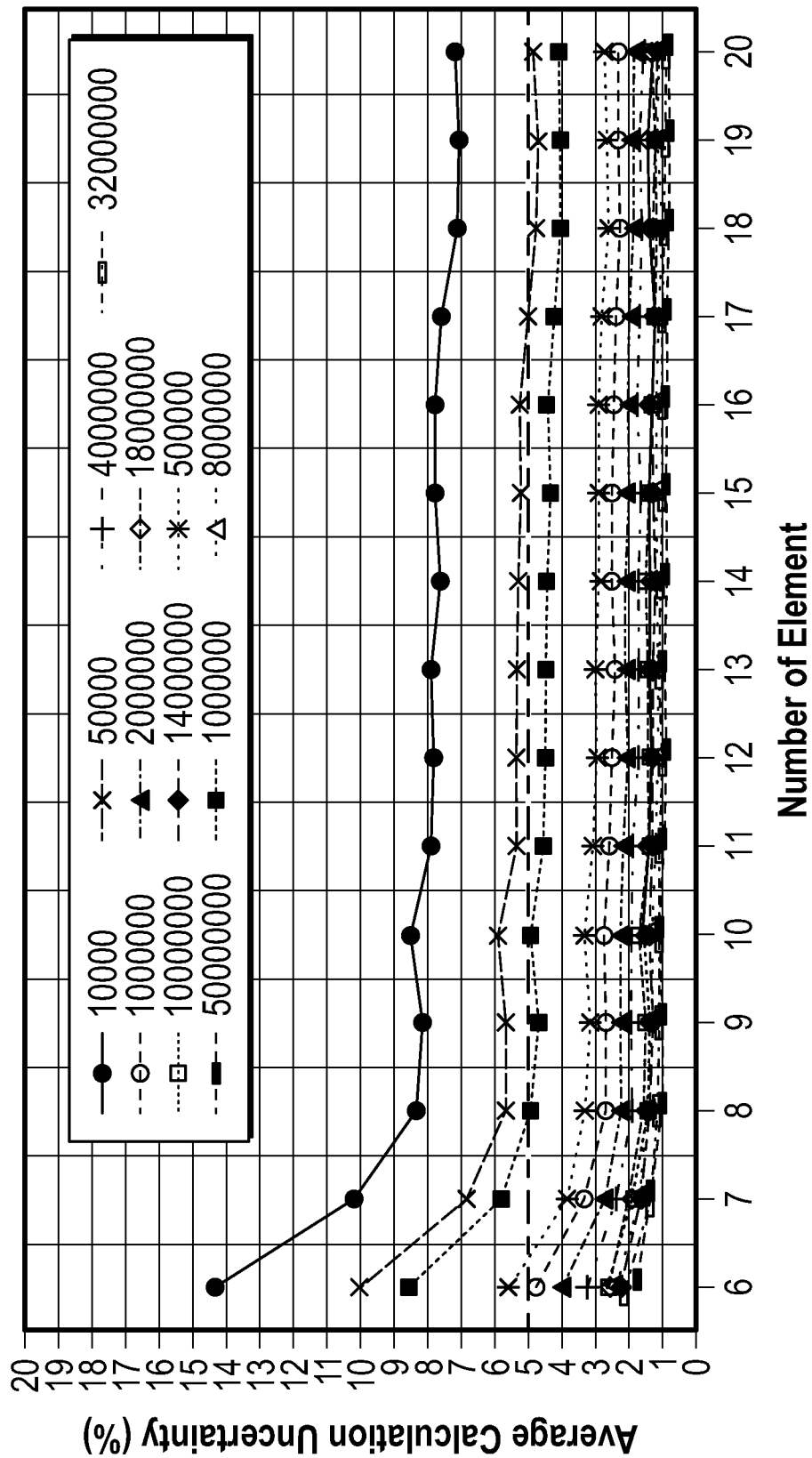
FIG. 12 is a graph depicting average calculation uncertainties for different numbers of analytes (6-20) for different values of Nrand, respectively in accordance with the present disclosure.
Figure 13:
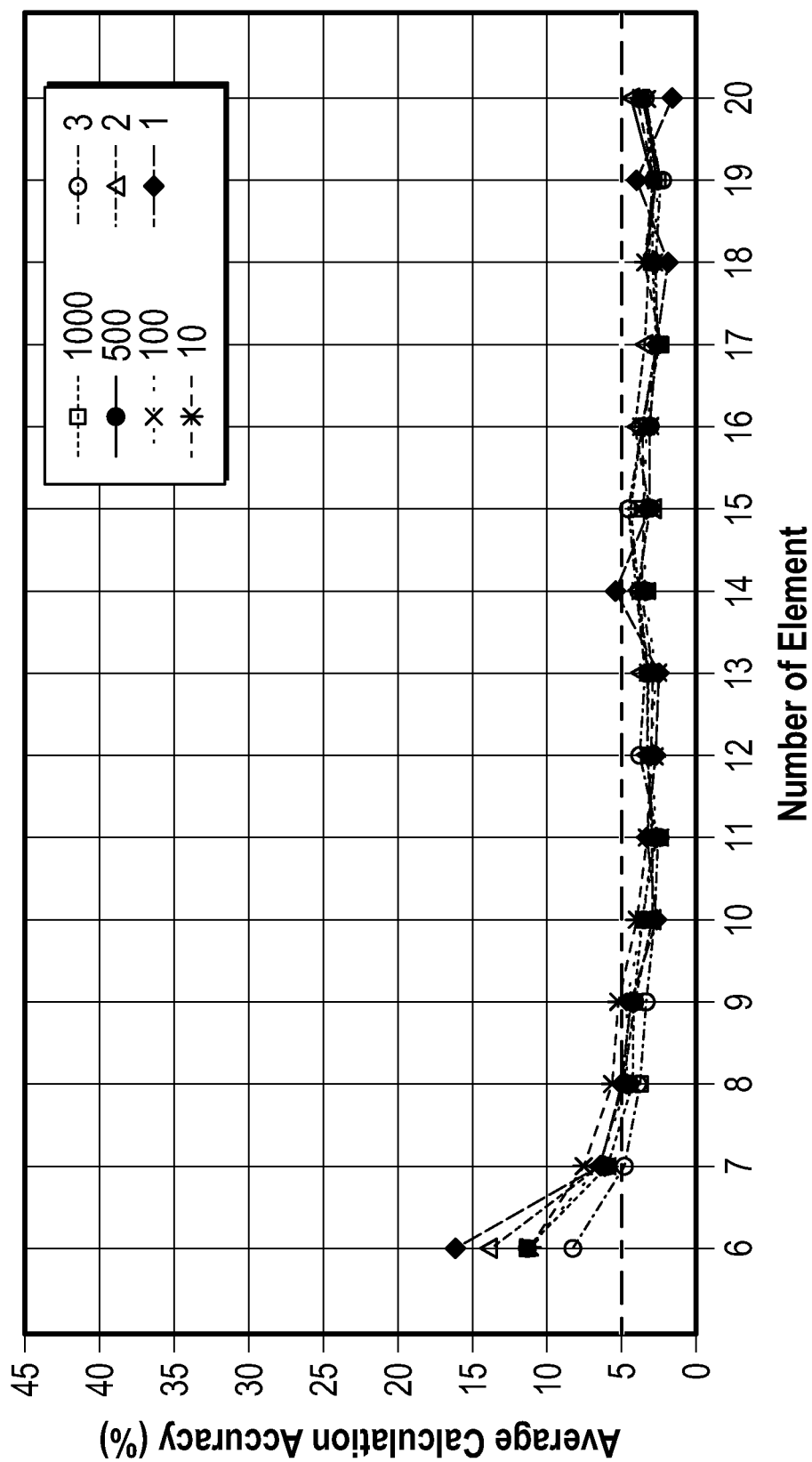
FIG. 13 is a graph depicting average calculation accuracies for different numbers of analytes (6-20) for a predefined multiple times of calculation (Ntime)=1,000, 500, 100, 10, 3, 2, and 1, respectively in accordance with the present disclosure.
Figure 14:
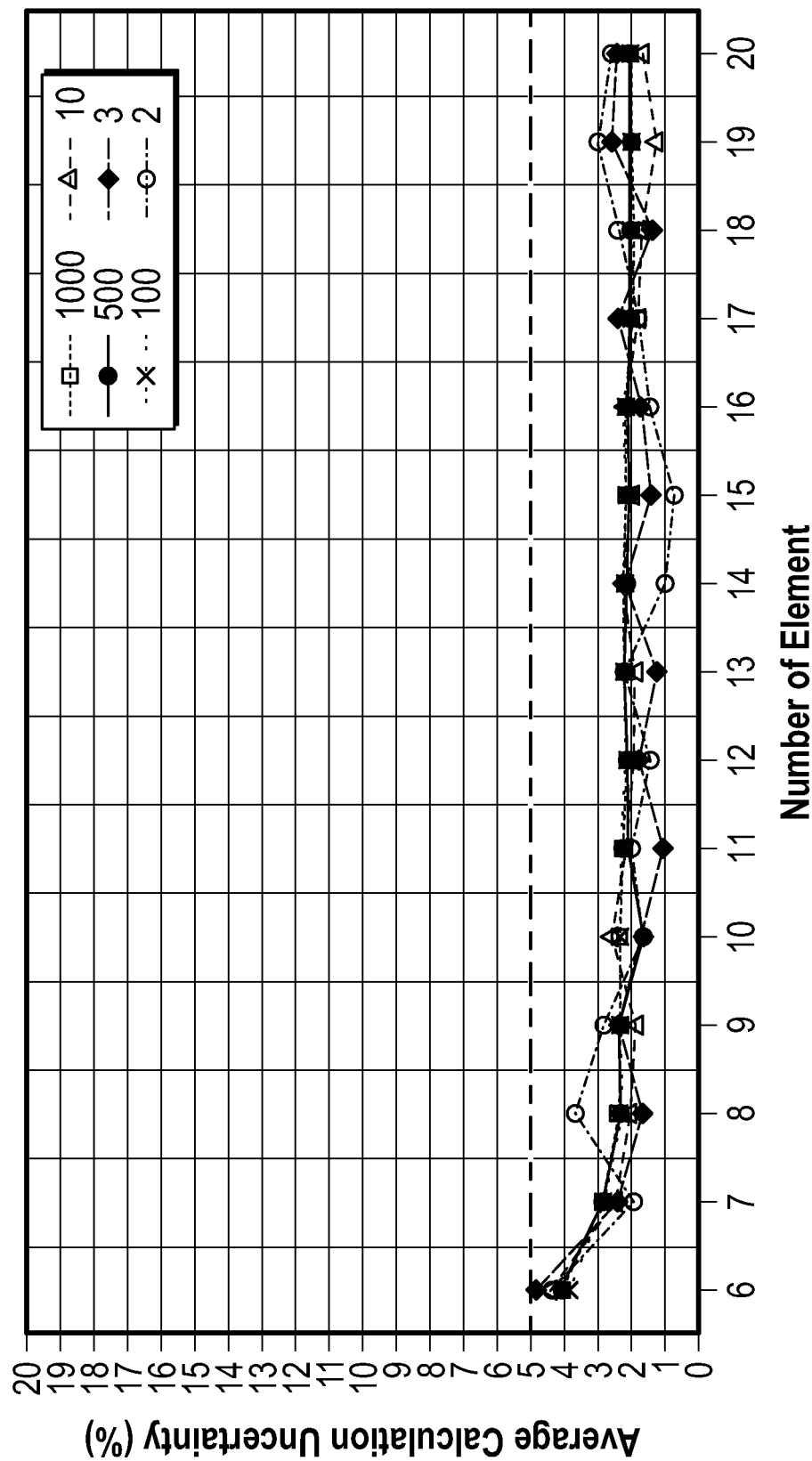
FIG. 14 is a graph depicting average calculation uncertainties for different numbers of analytes (6-20) for Ntime=1,000, 500, 100, 10, 3, 2, and 1, respectively in accordance with the present disclosure.
Figure 15:
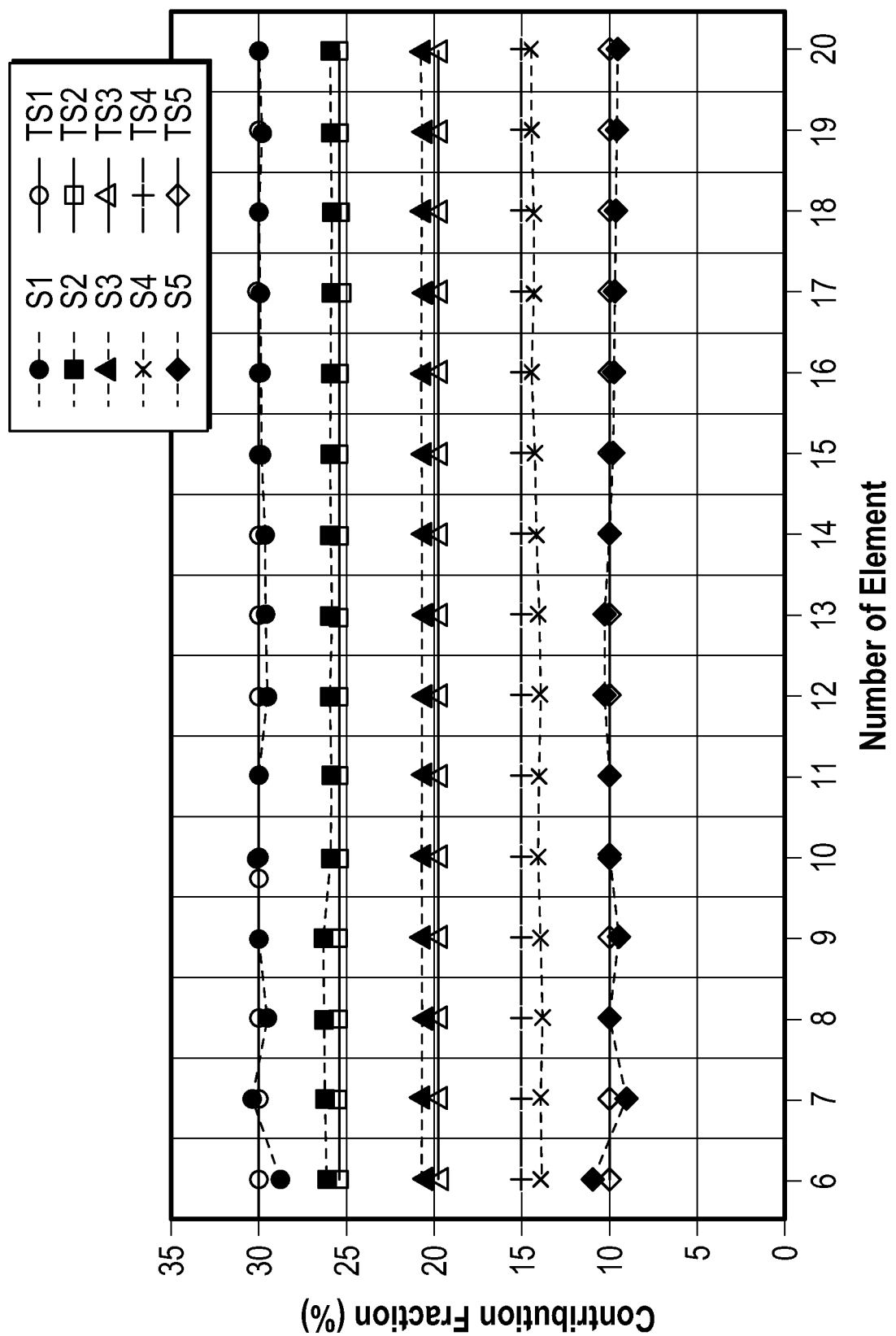
FIG. 15 is a graph depicting contribution fractions for different numbers of analytes for the relative standard deviation variation ($RSD_V$) Sort 1 (highest to lowest) in accordance with the present disclosure.

To test the influence of the first two potential factors to the results, the Nrand and Ntime were kept constant (Ntime=100; Nrand=2,000,000). Each of the 20 selected analytes has six ERSDs (S1-S5 and the commingled oil) (Table 1). The average ERSD of the six ERSDs of each analyte was calculated based on replicate analyses. At first, the 20 selected analytes were sorted from the lowest average ERSD to the highest average ERSD (ERSD Sort 1). Then, the determined mass fractions of the first six, seven, eight, and all the way to the twenty selected analytes were input into the program for a series of individual allocation calculations (A6-A20), respectively. The output contribution fractions, the corresponding calculation accuracies are shown in FIGS. 20 and 21, and the corresponding calculation uncertainties are summarized in FIGS. 6 and 7. Then, the 20 selected analytes were sorted from the highest average ERSD to the lowest average ERSD (ERSD Sort 2). The first six, seven, eight, and all the way to twenty out of the twenty selected analytes were used to conduct another series of individual allocation calculations, respectively. The results are summarized in FIGS. 8 and 22-24. As FIG. 9 indicates, generally, the average calculation accuracies are improved with the increasing numbers of analytes for both sorting strategies of the average ERSDs. However, beyond a certain number of analytes (11 for ERSD Sort 1 and 14 for ERSD Sort 2), the average accuracies start to become more stable. It is noted that the ERSD Sort 1 from lowest to highest obtained better average calculation accuracies and better corresponding SDs (bold error bars) for almost all the numbers of analytes when compared to the ERSD Sort 2 highest to lowest (FIG. 9). When the number of analytes utilized is more than eight, the average calculation accuracies can be less than 5% for ERSD Sort 1, whereas for ERSD Sort 2, only if the number of analytes utilized is more than 12, the average calculation accuracies can be below 5%. Thus Sort 1 converges to a more accurate result more quickly. FIG. 10 shows that the ERSD Sort 2 has a much higher average calculation uncertainty than ERSD Sort 1 when only six analytes are used for calculation. However, when more than six analytes are used, the average calculation uncertainties for both ERSD Sort 1 and 2 can be less than 3%, and for certain numbers of analytes used, the average calculation uncertainties for both sorting strategies are approximately identical. The number of calculations for each allocation run was optimized. To test the influence of Nrand to the results, Ntime was kept constant (Ntime=100), and ERSD Sort 1 was applied. The values of 10,000, 50,000, 100,000, 500,000, 1,000,000, 2,000,000, 4,000,000, 8,000,000, 10,000,000, 14,000,000, 18,000,000, 32,000,000, and 50,000,000 were tested for Nrand, respectively, and when Nrand was 50,010,000, the program crashed as the computer was out of memory. Thus, increasing Nrand does not enhance the average calculation accuracies (FIG. 11), whereas increasing Nrand did benefit by enhancing the average calculation uncertainties considerably (FIG. 12). Also, when a higher Nrand was used, a lower number of analytes is required to obtain an average calculation uncertainty below about 5%. The 13 tested values of Nrand were tested for Ntime=1, 2, 3, 10, 100, 500, and 1,000, respectively, for both ERSD Sort 1 and 2, and the same conclusion was reached. To test the influence of Ntime to the results, Nrand was kept constant (Nrand=2,000,000), and ERSD Sort 1 was applied. The values of about 1,000, 500, 100, 10, 3, 2, and 1 were tested for Ntime, respectively. Based on FIGS. 10 and 11, it is evident that the value of Ntime has little influence on both the average calculation accuracies and the corresponding average calculation uncertainties. However, the shape of the lines of average calculation accuracies and uncertainties is becoming increasingly curved with the decrease of Ntime (FIGS. 13 and 14). All calculation uncertainties are zero when Ntime=1, because all calculation SDs are zero (Eq. (3)). Therefore, a minimum of three for Ntime should be used to calculate the calculation uncertainties.

In summary, under the same conditions, 1) larger numbers of analytes are better than smaller numbers; 2) ERSD Sort 1 is better than ERSD Sort 2; 3) higher Nrand is better than lower Nrand; and 4) the value of Ntime has little influence on the results. The values of Nrand could be even higher than about 50,000,000 for the analysts to achieve lower calculation uncertainties if a computer with adequate speed and memory is employed. The higher the values for Nrand, the longer time required to run the program on any personal computer. The running time is primarily subject to the numbers of analytes used, Nrand, Ntime, and the conditions of the hardware configuration of the computer. However, a single run of the program if the number of analytes is 20, Nrand is 50,000,000, and Ntime is 100 for a simple personal computer (PC) takes about 29 min, and less than one min if the number of analytes is about 20, Nrand is about 2,000,000, and Ntime is 100. The results can be obtained immediately for a single run of the program if the number of analytes is about 6, Nrand is about 10,000, and Ntime is about 1.

Example 2

Figure 16:
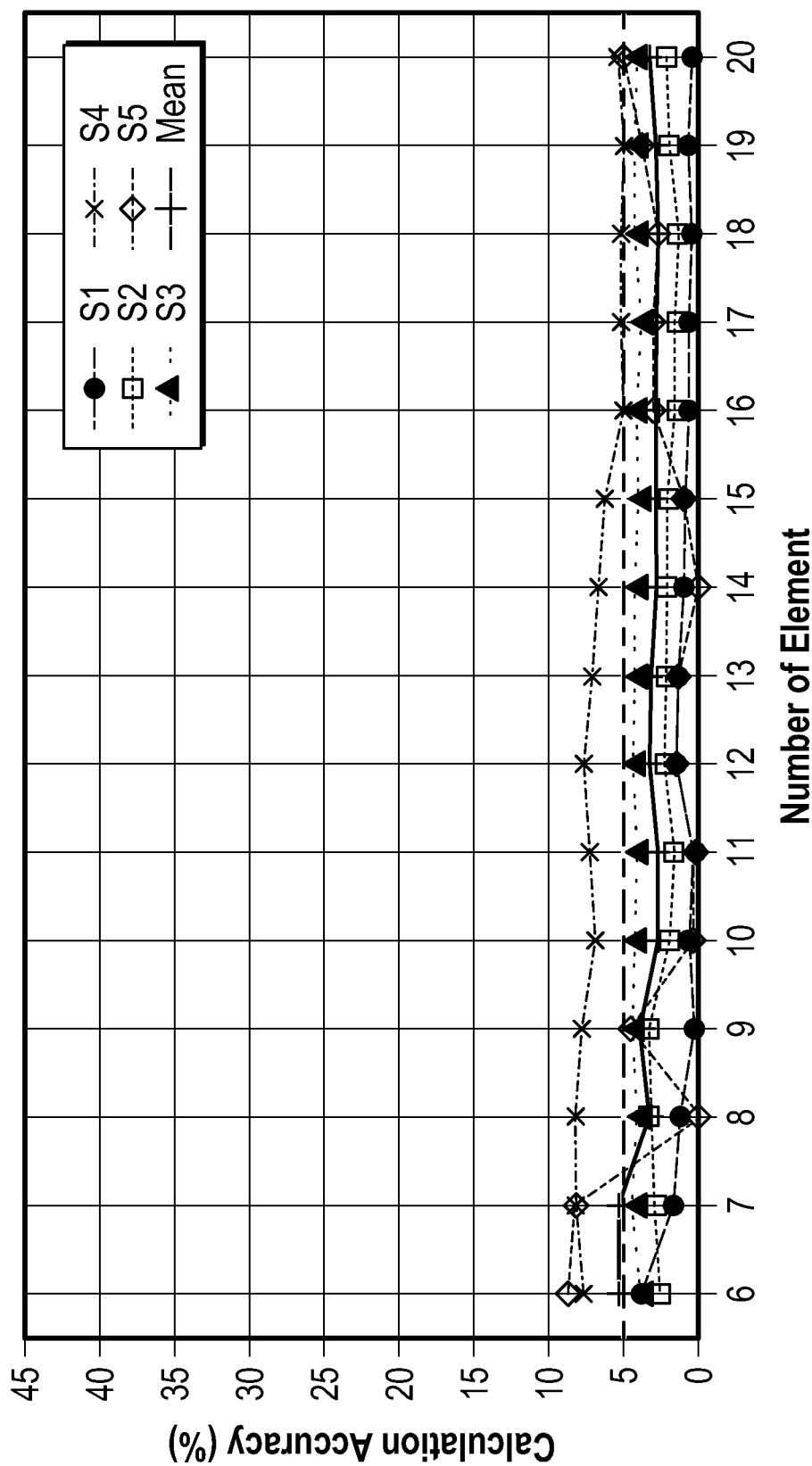
FIG. 16 is a graph depicting calculation accuracies for different numbers of analytes (6-20) for the $RSD_V$ Sort 1 (highest to lowest) in accordance with the present disclosure.
Figure 17:
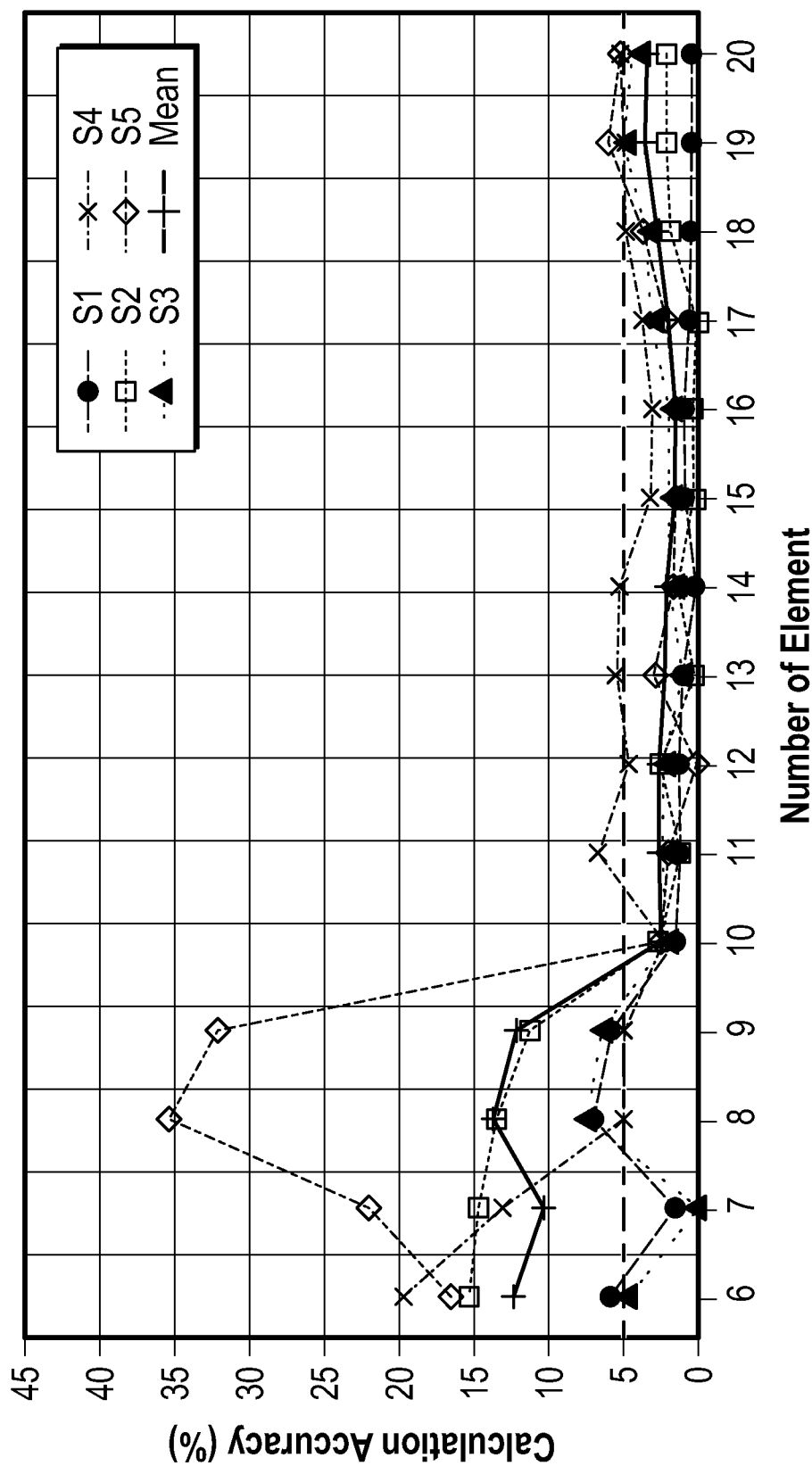
FIG. 17 is a graph depicting calculation accuracies for different numbers of analytes (6-20) for the $RSD_V$ Sort 2 (lowest to highest) in accordance with the present disclosure.

To test whether there is an effect of the abundance variations (variability) between the mass fractions of the five end-member oils and commingled oil for certain elements in terms of its importance in improving the calculation accuracies of the end-member contribution fractions, the analytes were sorted by variations from the highest to lowest (relative standard deviation variation ($RSD_V$) Sort 1) and lowest to highest ($RSD_V$ Sort 2), respectively. The Nrand and Ntime were kept constant (Ntime=100; Nrand=2,000,000). The initial supposition was that higher variabilities of analytes among the end members and commingled oil would enhance or improve solutions with lower number of elements. The variations can be given by the following Equation 4:

$$RSD_V=(SD/Mean)*100\%$$

where $RSD_V$ refers to the variation, SD refers to the standard deviation (1σ, n=6) of the mass fractions of the five end-member oils and commingled oil for a certain analyte, and Mean represents the average mass fraction of the five end-member oils and commingled oil for the same analyte. Then the first six, seven, eight, and all the way to twenty out of the twenty selected analytes were input into the program for allocation calculations for $RSD_V$ Sort 1 and Sort 2, respectively, and the results are summarized in FIGS. 15-17 and 26-28. The comparison between FIGS. 16 and 17 shows that $RSD_V$ Sort 1 obtained better calculation accuracies than $RSD_V$ Sort 2 for the numbers of elements 6-9, and gained close results compared to $RSD_V$ Sort 2 for the numbers of elements 10-20. For $RSD_V$ Sort 1, the pattern of calculation accuracies of the numbers of elements 6-16 is convergent, and the best results are achieved at the number of elements 16. When more than 15 (e.g., 16-20) elements are used for allocation calculations, the calculation accuracies keep stable with the increase of the numbers of elements, and almost all are below 5%. All calculation accuracies are below 10%. While for $RSD_V$ Sort 2, the calculation accuracies are poor for the numbers of elements 6-9. When more than about 9 (10-20) elements are used for allocation calculations, the calculation accuracies are within or close to 5%, and the best results are achieved with the number of elements of 16. Almost all the calculation uncertainties of RSDV Sort 1 and Sort 2 are below 10%, with most below 4% (FIGS. 27 and 28). Although generally $RSD_V$ Sort 1 is better than RSDV Sort 2, the two sorting methods achieved close results when more than 9 analytes were used for allocation calculations.

Figure 18:
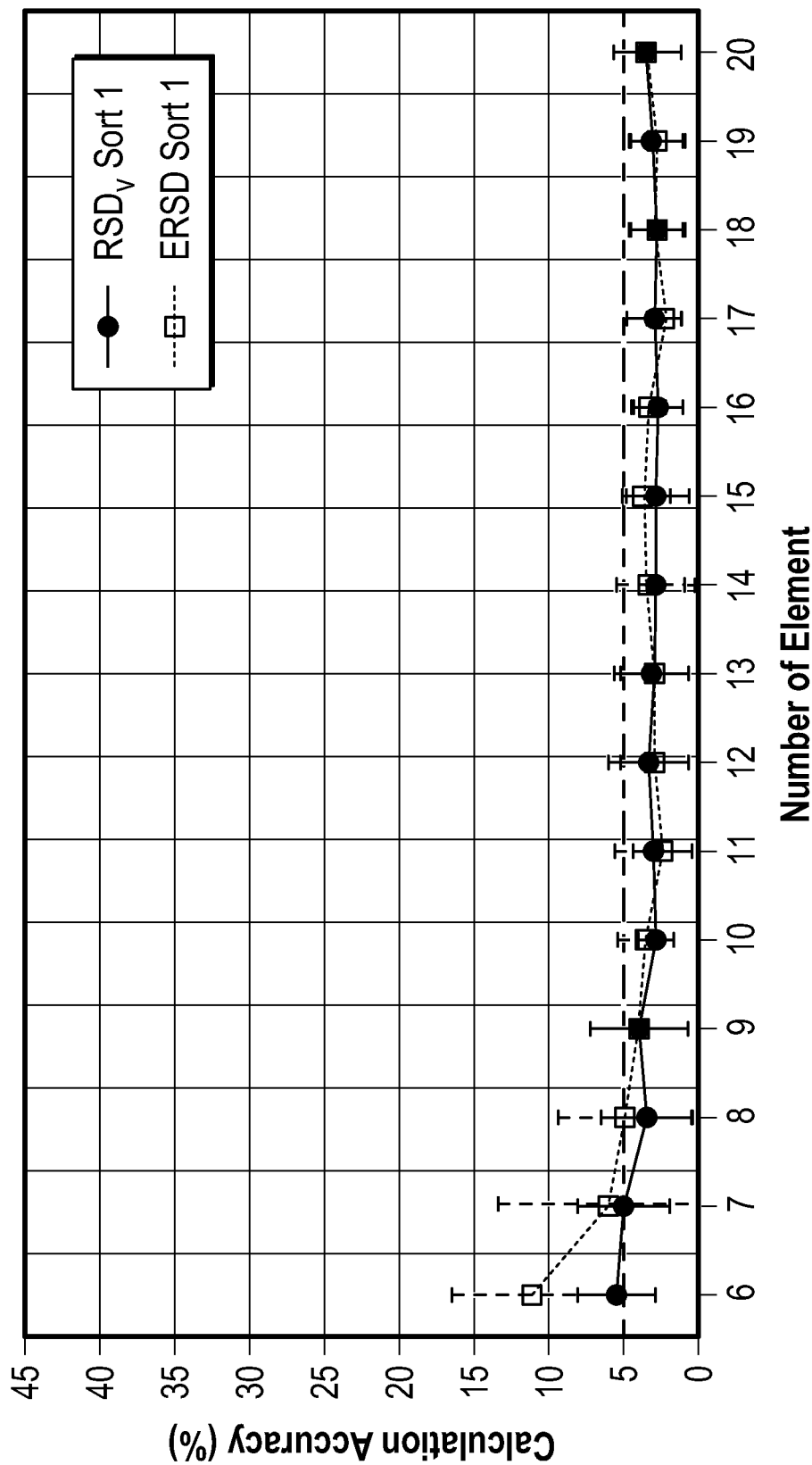
FIG. 18 is a graph depicting average calculation accuracies for different numbers of analytes (6-20) for the sorting methods of $RSD_V$ Sort 1 and ERSD Sort 1 in accordance with the present disclosure.

The sorting methods of ERSD Sort 1 and $RSD_V$ Sort 1 were compared (FIG. 18). The $RSD_V$ Sort 1 obtained better results only if less than about 9 (6-8) analytes were used for allocation calculations, and the two sorting methods were extremely close in allocation when more than about 8 (9-20) analytes were used. Therefore, the variations are shown to have an influence on the calculation accuracies only when less than about 10 analytes are used for calculations. Based on the analysis, more than about 10 analytes should be used for the allocation calculations to guarantee the best results, and thus the ERSD Sort 1 or $RSD_V$ Sort 1 are both adequate.

Based on the table shown in FIG. 21, when the numbers of analytes for calculations are not less than nine, the calculation accuracies of almost all the five end-member oils can be less than about 5.5%. Most calculation accuracies can be controlled lower than 4%, which is a good agreement between the calculated and actual contribution fractions of the five end-member oils. The best calculation accuracies for the five end-member oils (S1-S5) achieved in this study are 0.03%, 0.02%, 0.1%, 0.6%, and 0.1%, respectively (average 0.17% and median 0.1%). Based on the table shown in FIG. 22, almost all the corresponding calculation uncertainties are below 4%, and most are below 3%. The best calculation uncertainties for the five end-member oils (S1-S5) achieved in this study are 0.8%, 0.9%, 0.5%, 1.6%, and 2.3%, respectively (average 1.2% and median 0.9%). Therefore, this developed method is able to conduct production allocation calculations both accurately and precisely, and available to up to five end-member oils. The program ALLO-TRACE is efficient (less than one minute per run, generally to achieve precise and accurate results), and the program can be run many times in about twenty minutes to get a series of accurate and precise solutions using different numbers of analytes for estimates of allocation.

Example 3

The trace element crude oil fingerprinting production allocation methods described here provide rapid results (approximately 3 to approximately 4 days after sampling) for an accurate assessment. Oils from separate reservoirs or different parts of a reservoir may bear different chemical signatures or distinctive chemical fingerprints. These variations in petroleum composition may arise from one or a combination of compartmentalization of reservoirs, water washing, source maturity, source facies variation, oil biodegradation, charging and mixing of oils of different maturity or from different source rocks and in unconventional plays by variability in reservoir production levels and fracking penetrations.

Allocation assists with managing production and correctly reporting revenue to partners and government regulators. Production information at a sales meter, well, and/or subsurface completion level provide a basis 1) for financial aspects, which require production volumes from each well to calculate ownership and royalty interest to the owners of the mineral rights; 2) for the reservoir engineer to achieve updates of conventional or unconventional reservoir models with actual production and production changes calculated from each well; 3) for establishing production volumes that drive related areas such as decline analysis, stimulation, reservoir depletion planning and new well plans; and 4) for operation personnel that use the production volumes to manage the day-to-day activities against their production plan, with the allocated volumes driving processes such as forecasting, loss management, equipment management, optimization and constraint management.

In production allocation, having very frequent well tests and highly reliable meters installed with low error rates (less than about ±5%) connected via a digital network to a long-term storage device would allow efficient analysis and reporting of the collected data. However, because flow meters are often in continuous use, drifting can be a serious problem. Periodic meter proving may help identifying drift and correcting it. The cost of frequent well tests and the effort of maintaining fiscally accurate meters for every well in an operating asset, on the other hand, has proven challenging and can be prohibitively expensive. In some cases, frequent well tests are practically impossible (e.g., deviated and offshore wells). Generally, the number of metered points in a network always tends to decrease over the life of a field since replacement of damaged gauges becomes increasingly less economic and viable as the field's production declines, especially in unconventional reservoirs where declines are rapid and start soon after completion. Therefore, allocation calculations in these situations are usually designed to take into account degrading information quality and less accurate results over time. Trace element geochemical production allocation in accordance with the present methods, like its counterpart organic peak height or peak ratio Geo-chemical Production Allocation, provides the potential for a new, independent, and cost-efficient complement or alternative means for accurate production allocation, and field and well monitoring, provided accurate and precise trace element data, can be collected at frequent intervals from well sampling sites 122a, 122b, 122c (FIG. 1B) or key points of sale in the commingled production network. The present method can also simply complement production metering methods or infrequent production well tests in providing a low-cost method when higher frequency of allocation is important, when metering is not available or well-calibrated, or when well tests are unfeasible or too widely spaced in time for accurate allocation. In aspects, the present trace element method may also be applied potentially to other kinds of oils when the potential of measuring clear molecular biomarkers (e.g., condensates and biodegraded oils) is low and cannot easily achieve allocation.

Geochemical production allocation for oil wells in accordance with the present disclosure generally has several outstanding advantages compared to the conventional production logging method. The cost of geochemical production allocation based on organic geochemistry is commonly projected to be less than about 5% of more costly production logging. The trace multi-element geochemical method described herein involves a departure from organic geochemical techniques. Trace elemental abundance analyses, and allocation costs are about $1,000 (two end-members) to about $2,500 (five end-members) per well per allocation coupled with minimal sampling costs, while the alternative (production well logging) usually costs > about $60,000 per well per allocation (e.g., measured on a per month or per year basis). The trace element method may lower costs to about 1-2% or less of conventional logging flow tests that require shut down and production losses for multiple wells. The total yearly cost will depend on the number of end members and the desired frequency of allocations, but there are rarely more than five end-members per well per allocation. On a cost-basis, geochemical production allocation enables analysts to monitor the production more frequently than production logging, so production problems can be noticed, resolved, and remediated in a timely manner. Geochemical allocations can be applied to all kinds of wells, while generally, logging tools can only be applied to vertical wells or mildly deviated wells. The calculations of uncertainties for geochemical approaches are easier for geochemical techniques because of the ability to conduct replicate tests and thus obtain a series of independent solutions. Finally, compared to conventional techniques, geochemical sampling techniques are faster and incur no shutdown-related costs.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

Additionally, certain aspects of the present disclosure may include some, all, or none of the above advantages and/or one or more other advantages readily apparent to those skilled in the art from the drawings, descriptions, and claims included herein. Moreover, while specific advantages have been enumerated above, the various aspects of the present disclosure may include all, some, or none of the enumerated advantages and/or other advantages not specifically enumerated above.

The phrases "in an aspect," "in aspects," "in various aspects," "in some aspects," or "in other aspects" may each refer to one or more of the same or different aspects in accordance with the present disclosure. A phrase in the form "A or B" means "(A), (B), or (A and B)." A phrase in the form "at least one of A, B, or C" means "(A); (B); (C); (A and B); (A and C); (B and C); or (A, B, and C)."

What is claimed is:

1. A system for geochemical characterization of a sample, comprising:
    a closed reaction chamber configured to perform a high temperature and high-pressure acid digestion test on the sample;
    a spectrometry system configured for performing trace element analysis on the sample; and
    a controller including:
        a processor; and
        a memory including instructions stored thereon, which, when executed by the processor, cause the system to:
            mineralize the sample based on a microwave process using the closed reaction chamber, the microwave process including:
                monitoring a first temperature and a pressure inside the closed reaction chamber, and a second temperature of an outer wall of the closed reaction chamber;
                comparing the first temperature to a first threshold and the pressure to a second threshold; and
                controlling the first temperature and the second temperature based on the comparison; and
            perform trace element analysis on the sample by the spectrometry system.

2. The system of claim 1, wherein mineralizing the sample includes performing an acid digestion test at a predetermined temperature and a predetermined pressure.

3. The system of claim 1, wherein the trace element analysis includes performing inductively coupled plasma-optical emission spectrometry (ICP-OES) to analyze for major and minor elements.

4. The system of claim 3, wherein the trace element analysis further includes performing inductively coupled plasma-mass spectrometry (ICP-MS) to analyze for low-abundance trace elements.

5. The system of claim 1, wherein the sample includes at least one of a food-grade oil, or subsurface rock.

6. The system of claim 1, wherein the sample includes a hydrocarbon, and
    wherein the instructions, when executed by the processor, further cause the system to monitor a well for at least one of a decline or a downhole blockage during production operations based on the trace element analysis of the hydrocarbon sample.

7. The system of claim 5, wherein the instructions, when executed by the processor, further cause the system to:
    correlate the sample to a second sample based on the trace element analysis; and
    determine at least one of a country origin, oil field origin, or source rock origin of the sample of the hydrocarbon sample.

8. The system of claim 2, wherein prior to performing the trace element analysis, the instructions, when executed by the processor, further cause the system to:
    dry the sample;
    re-dissolve the digested sample; and
    dilute the sample.

9. The system of claim 1, wherein the instructions, when executed by the processor, further cause the system to:
    determine a unique fingerprint based on the trace element analysis of the sample; and
    display, on a display, the unique fingerprint.

10. A computer-implemented method for geochemical characterization of a sample, the method comprising:
    controlling a system comprising:
        a closed reaction chamber configured to perform a high temperature and high-pressure acid digestion test on the sample;
        a spectrometry system configured for performing trace element analysis on the sample;

mineralizing the sample via a microwave process using the closed reaction chamber, the microwave process including:
monitoring a first temperature and a pressure inside the closed reaction chamber, and a second temperature of an outer wall of the closed reaction chamber;
comparing the first temperature to a first threshold and the pressure to a second threshold; and
controlling the first temperature and the second temperature based on the comparison; and
performing trace element analysis, after mineralizing the sample, via inductively coupled plasma mass spectrometry by the spectrometry system.

11. The method of claim 10, wherein the sample includes at least one of a food-grade oil, or subsurface rock.

12. The method of claim 10, wherein mineralizing the sample is based on a microwave process using a closed reaction chamber configured to perform a high temperature and high-pressure acid digestion test.

13. The method of claim 10, wherein mineralizing the sample includes performing an acid digestion test at a predetermined temperature and a predetermined pressure.

14. The method of claim 10, wherein the trace element analysis is performed by a triple-quadrupole mass spectrometry (TQMS) system.

15. The method of claim 10, wherein the trace element analysis includes performing inductively coupled plasma-optical emission spectrometry (ICP-OES) to analyze for major and minor elements.

16. The method of claim 10, wherein the trace element analysis further includes performing inductively coupled plasma-mass spectrometry (ICP-MS) to analyze for low-abundance trace elements.

17. The method of claim 10, further comprising:
determining a unique fingerprint based on the trace element analysis of the sample; and
displaying, on a display, the unique fingerprint.

18. The method of claim 11, further comprising, prior to performing the trace element analysis:
drying the sample;
re-dissolving the digested sample; and
diluting the sample.

19. The method of claim 18, further comprising:
correlating the sample to a second sample based on the trace element analysis, wherein the sample includes a hydrocarbon sample; and
determining at least one of a country origin, oil field origin, or source rock origin of the sample of the hydrocarbon sample.

20. A non-transitory computer-readable storage medium in which is stored a program for causing a computer to execute a computer-implemented method for geochemical characterization of a sample, the method comprising:
mineralizing the sample via a microwave process, the microwave process including:
monitoring a first temperature and a pressure inside the closed reaction chamber, and a second temperature of an outer wall of the closed reaction chamber;
comparing the first temperature to a first threshold and the pressure to a second threshold; and
controlling the first temperature and the second temperature based on the comparison; and
performing trace element analysis on the mineralized sample via inductively coupled plasma mass spectrometry.

* * * * *